(12) United States Patent
Itkowitz et al.

(10) Patent No.: US 11,406,462 B2
(45) Date of Patent: Aug. 9, 2022

(54) TELEOPERATED SURGICAL SYSTEM WITH SCAN BASED POSITIONING

(71) Applicant: Intuitive Surgical Operations, Inc., Sunnyvale, CA (US)

(72) Inventors: Brandon D. Itkowitz, San Jose, CA (US); Mahdi Azizian, Santa Clara, CA (US); Brian D. Hoffman, Mountain View, CA (US); Ian E. McDowall, Woodside, CA (US); Paul W. Mohr, Mountain View, CA (US); William C. Nowlin, Los Altos Hills, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 327 days.

(21) Appl. No.: 16/349,214

(22) PCT Filed: Nov. 10, 2017

(86) PCT No.: PCT/US2017/061144
§ 371 (c)(1),
(2) Date: May 10, 2019

(87) PCT Pub. No.: WO2018/089823
PCT Pub. Date: May 17, 2018

(65) Prior Publication Data
US 2020/0188047 A1 Jun. 18, 2020

Related U.S. Application Data

(60) Provisional application No. 62/421,089, filed on Nov. 11, 2016.

(51) Int. Cl.
*A61B 34/35* (2016.01)
*A61B 34/10* (2016.01)
(Continued)

(52) U.S. Cl.
CPC .............. *A61B 34/35* (2016.02); *A61B 34/10* (2016.02); *A61B 34/37* (2016.02); *A61B 34/70* (2016.02);
(Continued)

(58) Field of Classification Search
CPC ......... A61B 34/35; A61B 34/10; A61B 34/37; A61B 34/70; A61B 90/361; A61B 90/50;
(Continued)

(56) References Cited

U.S. PATENT DOCUMENTS

| 5,446,548 A | 8/1995 | Gerig et al. |
| 5,919,135 A | 7/1999 | Lemelson |

(Continued)

FOREIGN PATENT DOCUMENTS

| CN | 102933163 A | 2/2013 |
| EP | 3503831 A1 | 7/2019 |

(Continued)

OTHER PUBLICATIONS

International Preliminary Report on Patentability for Application No. PCT/US2017/061144, dated May 23, 2019, 11 pages.
(Continued)

*Primary Examiner* — Richard G Louis
(74) *Attorney, Agent, or Firm* — Schwegman Lundberg & Woessner, P.A.

(57) ABSTRACT

A method is provided for use with a teleoperated surgical system, the method comprising: determining patient position information during a setup for a performance of the surgical procedure within an instance of the surgical system; determining a match between the determined patient position and a patient position signature; and launching a support arm control signal within the surgical system that corresponds to the matched support arm signature.

10 Claims, 16 Drawing Sheets

(51) Int. Cl.
  *A61B 34/37* (2016.01)
  *A61B 34/00* (2016.01)
  *A61B 90/00* (2016.01)
  *A61B 90/50* (2016.01)
  *A61B 50/13* (2016.01)
  *A61B 17/00* (2006.01)
  *B25J 9/16* (2006.01)
  *A61B 50/33* (2016.01)
  *A61B 46/10* (2016.01)

(52) U.S. Cl.
  CPC ............ *A61B 90/361* (2016.02); *A61B 90/50* (2016.02); *A61B 46/10* (2016.02); *A61B 50/13* (2016.02); *A61B 50/33* (2016.02); *A61B 2017/00477* (2013.01); *A61B 2034/107* (2016.02); *A61B 2034/256* (2016.02); *B25J 9/1689* (2013.01)

(58) Field of Classification Search
  CPC .......... A61B 46/00; A61B 2017/00477; A61B 2034/256; A61B 50/33; A61B 46/10; A61B 2034/107; A61B 50/13; A61B 2090/061; A61B 34/32; A61B 90/74; A61B 90/06; B25J 9/1689
  See application file for complete search history.

(56) References Cited

U.S. PATENT DOCUMENTS

| | | |
|---|---|---|
| 6,109,270 A | 8/2000 | Mah |
| 6,491,702 B2 | 12/2002 | Heilbrun et al. |
| 8,837,791 B2 | 9/2014 | Plakas et al. |
| 2007/0270685 A1* | 11/2007 | Kang .................. A61B 17/1764 600/424 |
| 2014/0148816 A1 | 5/2014 | McDonald et al. |
| 2015/0065803 A1 | 3/2015 | Douglas et al. |
| 2016/0151120 A1* | 6/2016 | Kostrzewski .......... A61B 90/50 606/130 |
| 2018/0110573 A1* | 4/2018 | Kostrzewski .......... B25J 9/1679 |
| 2018/0185103 A1* | 7/2018 | Mukumoto ............ B25J 9/1697 |

FOREIGN PATENT DOCUMENTS

| | | |
|---|---|---|
| JP | 2012005557 A | 1/2012 |
| WO | WO-9833451 A1 | 8/1998 |
| WO | WO-2015003748 A1 | 1/2015 |
| WO | WO-2015142955 A1 | 9/2015 |
| WO | WO-2017030848 A1 | 2/2017 |

OTHER PUBLICATIONS

International Search Report and Written Opinion for Application No. PCT/US2017/061144, dated Feb. 19, 2018, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP17870051.4 dated Sep. 9, 2020, 13 pages.

Buzurovic., I., et al., "Force Prediction and Tracking for Image-guided Robotic System using Neural Network Approach," Biomedical Circuits and Systems Conference, Nov. 2008, pp. 41-44, XP031398798.

Partial Supplementary European Search Report for Appiication No. 17870051.4, dated Jun. 9, 2020, 17 pages

* cited by examiner

TELEOPERATED SURGICAL SYSTEM WITH SCAN BASED POSITIONING

CLAIM OF PRIORITY

This application is a U.S. National Stage Filing under 35 U.S.C. 371 from International Application No. PCT/US2017/061144, filed on Nov. 10, 2017, and published as WO 2018/089823 A1 on May 17, 2018, which claims the benefit of priority to U.S. Patent Application No. 62/421,089, filed on Nov. 11, 2016, each of which is hereby incorporated by reference herein in its entirety.

BACKGROUND

1. Field of Invention

Inventive aspects are associated with medical devices used during surgery. More specifically, aspects are associated with positioning of surgical system components.

2. Art

Surgeons typically undertake extensive study before performing a surgical procedure. Traditionally, surgeons were limited to the study of generic anatomical models, such as photographs or drawings. More recently, various pre-operative diagnostic procedures (e.g., x-ray, CT, MRI, etc.) have made patient-specific anatomical information available.

In some cases, it is desirable to make additional, relevant anatomic and surgical procedure information available to a surgeon. In one aspect, it is desirable to provide a surgeon planning an operation on a particular patient with a surgical site video recording of an earlier surgical procedure performed on the particular patient. In another aspect, it is desirable to provide a surgeon with one or more surgical video recordings of surgical procedures on other patients that are similar to the surgical procedure planned for a particular patient. In one aspect, it is desirable to provide such information to a surgeon prior to the surgeon undertaking a particular surgical procedure. And in another aspect, it may be desirable to provide this information to a surgeon intraoperatively.

In one aspect, it is desirable to configure a video database that includes intraoperative surgical site video recordings of various procedures undergone by various patients. In one aspect, it is desirable to configure a medical device capable of video recording to further include an input that enables a surgeon using the medical device to highlight and annotate the video recording in real time as it is being recorded. In one aspect, it is desirable to configure a computer-based pattern matching algorithm to search through the individual records of the video database, identify relevant video records, and provide a surgeon with this relevant information for a particular surgical procedure.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

In one aspect, a method is provided for use with a teleoperated surgical system. Patient position information is determined during a setup of the surgical system for a surgical procedure. A match is determined between the determined patient position information during the setup and a respective patient position signature. A support arm control signal is launched during the setup that corresponds to the matched respective patient position signature.

In another aspect, a method is provided for use with a teleoperated surgical system. Operating room layout is determined during a setup of the surgical system for a surgical procedure. A match is determined between the determined operating room layout during the setup and a respective operating room layout signature. An image is produced representing a surgical system module position that corresponds to the matched respective operating room layout signature.

DETAILED DESCRIPTION

Figure 1:
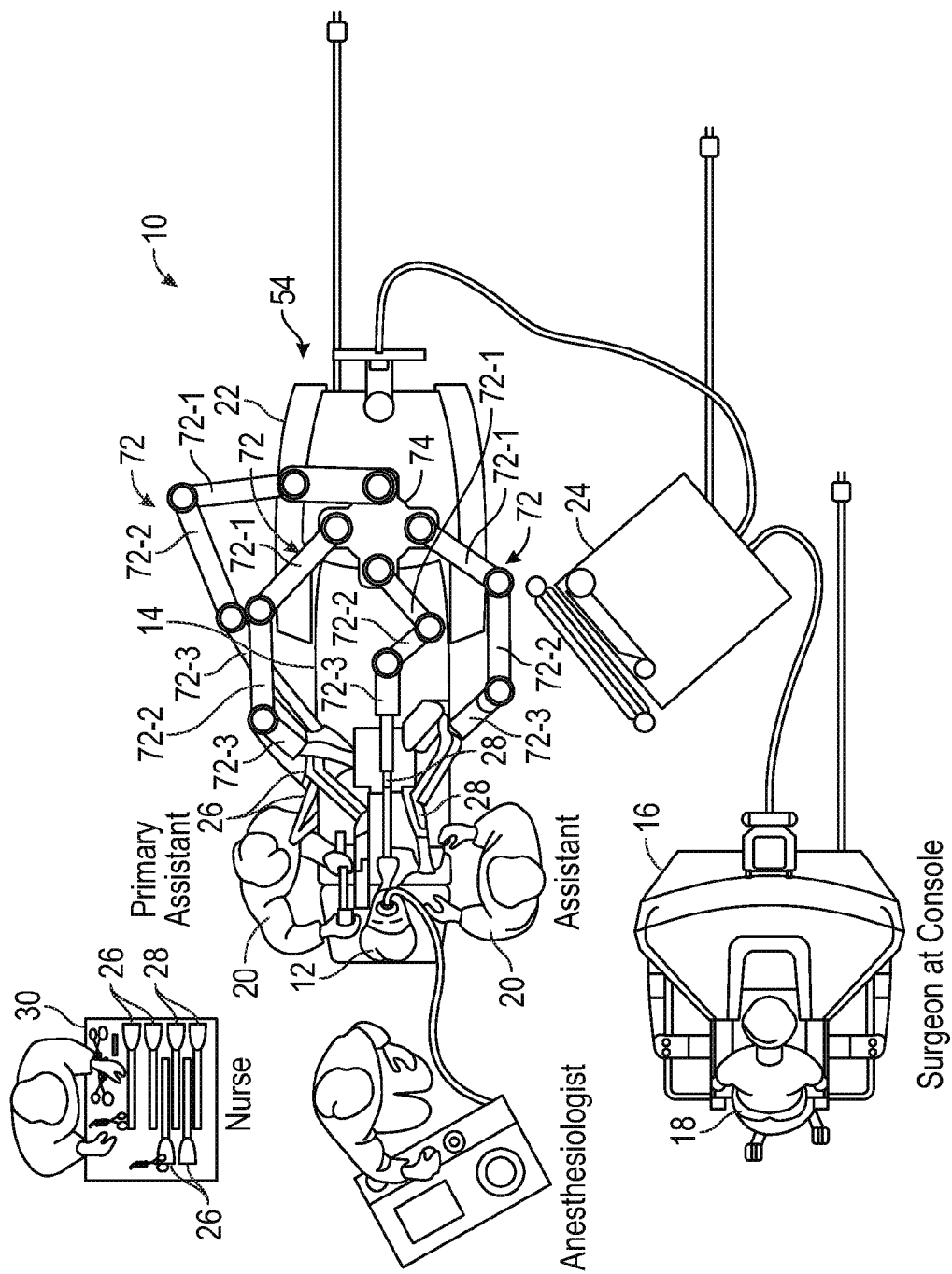
FIG. 1 is a plan view of a minimally invasive teleoperated surgical system.

This description and the accompanying drawings that illustrate inventive aspects, embodiments, implementations, or applications should not be taken as limiting the claims define the protected invention. Various mechanical, compositional, structural, electrical, and operational changes may be made without departing from the scope of this description and the claims. In some instances, well-known circuits, structures, or techniques have not been shown or described in detail in order not to obscure the invention. Like numbers in two or more figures represent the same or similar elements.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® Surgical System (specifically, a Model IS4000, marketed as the da Vinci® Xi™ HD™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000 da Vinci® Xi™ Surgical System, the Model IS3000 da Vinci Si® Surgical System) are merely exemplary and are not to be considered as limiting the scope of the inventive aspects disclosed herein.

In accordance with various aspects, the present disclosure describes a surgical planning tool that includes a medical device configured to video record the performance of surgical procedures. The video recordings can be embedded with various metadata, e.g., highlights made by a medical person. Additionally, the video recordings can be tagged with various metadata, e.g., text annotations describing certain subject matter of the video, the identity of the patient to whom the video recording corresponds, biographical or medical information about the patient, and the like. In one aspect, tagged metadata is embedded in the video recordings.

In accordance with further aspects, a robotic arm configured to mount a surgical instrument is positioned based at least in part upon position of at least one patient anatomical feature. In accordance with yet a further aspect, a cart-mounted robotic surgical system module can be positioned nearby to a patient based at least in part upon configuration of an operating room in which a surgical procedure is performed. During a teleoperated robot assisted surgical procedure, a surgical instrument extends through a surgical port at an incision in the patient's anatomy into the patient's body cavity. Incision location and surgical port location are determined based at least in part upon type of surgical procedure, dimensions of the patient's body and the patient's position on the surgical table. In some embodiments, a surgical instrument is positioned during surgery so as to have a center axis of rotation at the port so as to minimize strain on anatomical tissue surrounding the port.

In some embodiments, multiple cart-mounted surgical system module are disposed about a patient during a surgery. One or more of the surgical system modules includes a robotic surgical arm configured to mount a surgical instrument. In some embodiments, each of multiple robotic surgical arms mounts a different surgical instrument. During a surgical procedure, each instrument extends through a different surgical port to a different location within the patient's body cavity. Ordinarily, multiple medical personnel move about within an operating room during a surgery. The medical personnel must have ready access to the patient, both for routine surgical activities and to respond to emergencies. A surgical procedure may involve a sequence of surgical activities such as cutting, cauterizing and suturing, for example. Different surgical activities may require use of different surgical instruments or different combinations of surgical instruments. During the surgical procedure, medical personnel may be required to move between a patient and a cart-mounted surgical system module or between multiple cart-mounted surgical system modules, within an operating room to change surgical instruments extending through one or more of the surgical ports in order to reconfigure the teleoperated surgical system or to perform other surgical activities. For example, a surgical instrument used during one surgical activity can be removed when that surgical activity is completed and a different surgical instrument can be inserted in its place to perform a different surgical activity. An operating room in which a surgical procedure is performed may have limited space in which to position cart-mounted surgical system modules so as to afford ease of access to surgical ports while still allowing sufficient spacing between cart-mounted surgical system modules and a patient table or between such modules themselves, for medical personnel to freely and efficiently move about an operating room during a surgery.

Video recordings, information structures that associate robotic surgical arm positioning with patient position and/or with patient body characteristics such as height and weight, and information structures that associate surgical system module positioning with operating room layout, can be archived on an electronic medical record database implemented locally or on a cloud data storage service. The video recordings can be made available to interested health care providers. The information structures are used with a surgical system setup guidance to determine positioning of robotic surgical arms and of surgical system modules.

Health care providers can search the medical device database based upon one or more of surgical procedure to be performed, patient body characteristics and operating room layout for videos and information structure relationships of interest using the metadata tags described above. Additionally, in one aspect, the surgical planning tool includes a computer-based pattern matching and analysis algorithm. In one aspect, the pattern-matching algorithm culls through the videos stored on the electronic medical record database to identify correlations between visual characteristics in the video recordings and associated metadata tags made by medical persons. The surgical planning tool can apply these correlations to newly encountered anatomy, and thereby assist medical persons performing a procedure in making determinations about patient anatomy, preferred surgical approaches, disease states, potential complications, etc.

In another aspect, a pattern matching algorithm culls through videos and other recordings stored on the electronic medical record database to identify robotic surgical arm position setups that most suitable to different patient positions and anatomies. Moreover, a pattern matching algorithm culls through videos and other recordings stored on the electronic medical record database to identify surgical system module positions that promote the most efficient use of operating room space for different operating room layouts. In some embodiments, scanning device such as a light illumination scanning device a laser scanning device, an IR scanning device or an RF scanning device)) can be used to record patient body position and to record medical personnel movements. Alternatively or in addition, videos can provide a record of medical personnel movement during a surgical procedure. Alternatively, for example, tracking devices such as RFID tags can be worn by medical personnel to track their movements. Records of patient body position during previous surgeries can be used to determine the most efficient setup of one or more robotic surgical arms to more quickly achieve precise instrument positioning during surgical setup. Records of medical personnel movements during previous surgeries can be used to determine the most efficient setup of surgical system modules to facilitate ease and speed of medical personnel movement during a surgery.

Minimally Invasive Teleoperated Surgical System

Referring now to the drawings, in which like reference numerals represent like parts throughout the several views, FIG. 1 is a plan view of a minimally invasive teleoperated surgical system 10, typically used for performing a minimally invasive diagnostic or surgical procedure on a patient 12 who is lying on a mobile operating table 14. The system includes a mobile surgeon's console 16 for use by a surgeon 18 during the procedure. One or more assistants 20 may also participate in the procedure. The minimally invasive teleoperated surgical system 10 further includes a mobile patient-side cart 22 and a mobile electronics cart 24. In some embodiments, the table 14, surgeon's console 16, patient-side cart 22, and the electronics cart 24 are wheel mounted to provide mobility.

The patient-side cart 22 includes multiple segmented mechanical support arms 72, each having one end portion rotatable mounted to a vertical support structure 74 and having another end mounting a removably coupled surgical instrument 26. In some of embodiments, each mechanical support arm 72 includes a first segment 72-1, a second segment 72-2 and a third segment 72-3. During setup for a surgical procedure, the multiple segments of at least one support arm 72 are moved to position a surgical instrument for insertion within a minimally invasive incision in the body of the patient 12. During the surgical procedure, while surgical instruments are inserted within a patient's body cavity, the surgeon 18 views the surgical site through the surgeon's console 16, An image of the surgical site can be obtained by an endoscope 28, such as a stereoscopic endoscope, which can be manipulated by the patient-side cart 22 to orient the endoscope 28. Computer processors located on the electronics cart 24 can be used to process the images of the surgical site for subsequent display to the surgeon 18 through the surgeon's console 16. The number of surgical instruments 26 used at one time will generally depend on the diagnostic or surgical procedure and the space constraints within the operating room among other factors. If it is necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
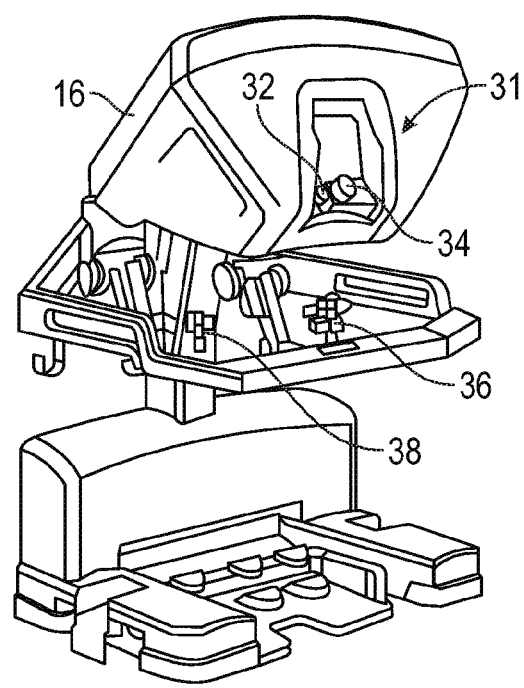
FIG. 2 is a perspective view of a surgeon's console.

FIG. 2 is a perspective view of the surgeon's console 16. The surgeon's console 16 includes a left eye display 32 and a right eye display 34 for presenting the surgeon 18 with a coordinated stereoscopic view of the surgical site that enables depth perception. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36.

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
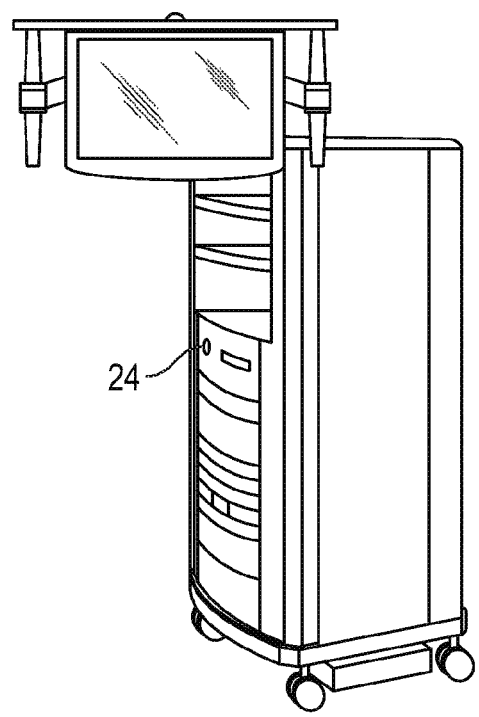
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
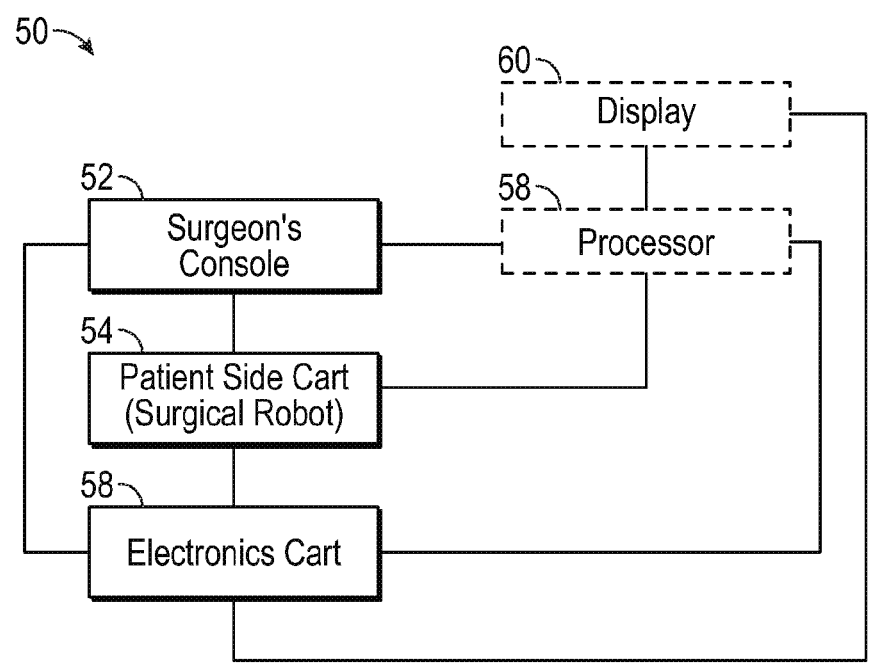
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). A surgeon's console 52 (such as surgeon's console 16 in FIG. 1) can be used by a surgeon to control a patient-side cart 54 (such as patent-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Additionally or in the alternative, the captured images can undergo image processing by a computer processor located outside of electronics cart 56. In one aspect, teleoperated surgical system 50 includes an optional computer processor 58 (as indicated by dashed line) similar to the computer processor located on electronics cart 56, and patient-side cart 54 outputs the captured images to computer processor 58 for image processing prior to display on the surgeon's console 52. In another aspect, captured images first undergo image processing by the computer processor on electronics cart 56 and then undergo additional image processing by computer processor 58 prior to display on the surgeon's console 52. Teleoperated surgical system 50 can include an optional display 60, as indicated by dashed line. Display 60 is coupled with the computer processor located on the electronics cart 56 and with computer processor 58, and captured images processed by these computer processors can be displayed on display 60 in addition to being displayed on a display of the surgeon's console 52.

Figure 5A:
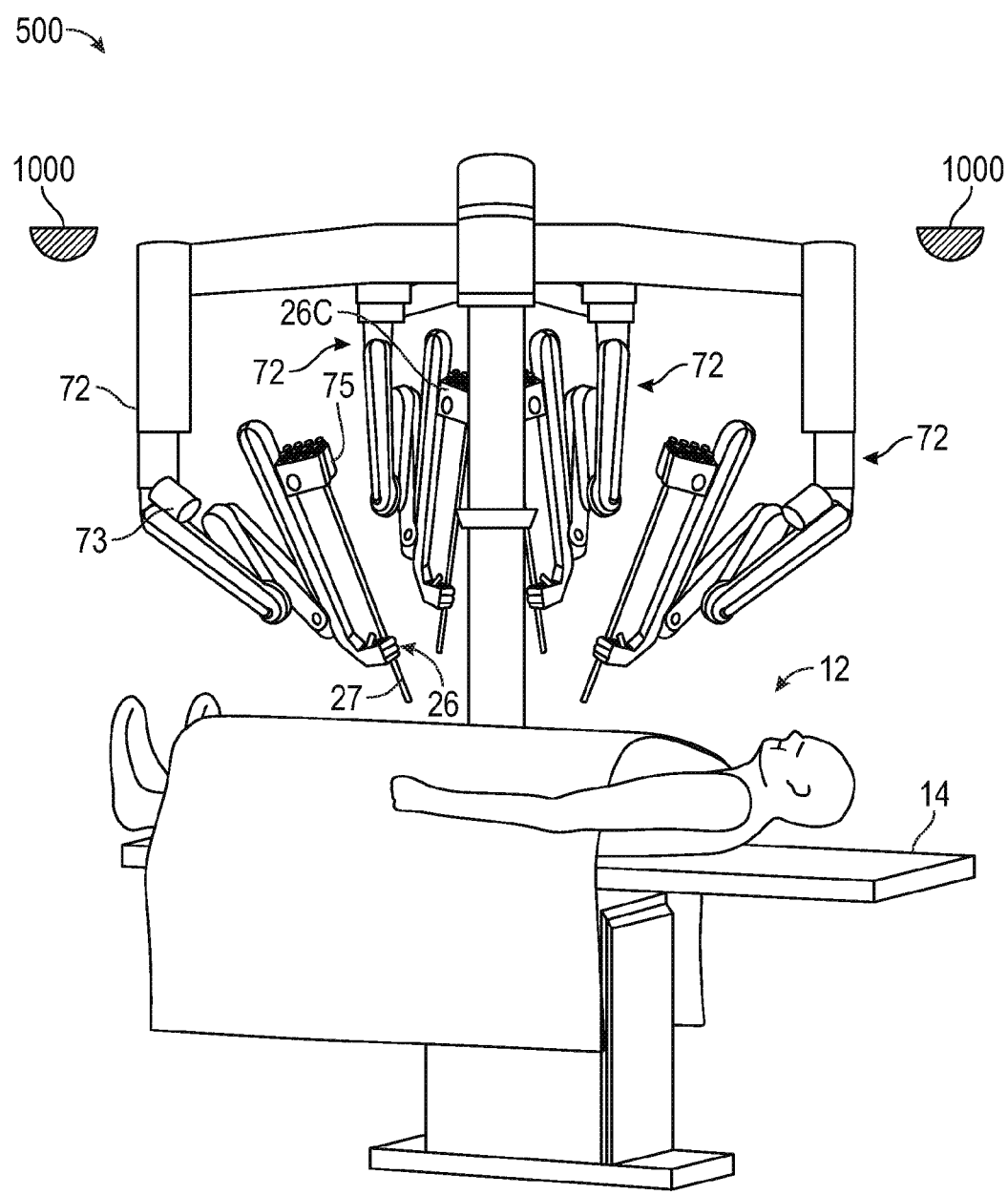
FIG. 5A is a perspective view of a patient-side cart of a minimally invasive teleoperated surgical system, in accordance with embodiments.

FIG. 5A is a perspective view of a patient-side cart 54 of a minimally invasive teleoperated surgical system 10, in accordance with embodiments. The patient-side cart 54 includes four mechanical support arms 72. A surgical instrument manipulator 73, which includes motors to control instrument motion, is mounted at the end of each support arm assembly 72. Additionally, each support arm 72 can optionally include one or more setup joints (e.g., unpowered and/or lockable) that are used to position the attached surgical instrument manipulator 73 with reference to the patient for surgery. As depicted, the patient-side cart 54 rests on the floor. In other embodiments, operative portions of the patient-side cart can be mounted to a wall, to the ceiling, to the operating table 14 that also supports the patient's body 12, or to other operating room equipment. Further, while the patient-side cart 54 is shown as including four surgical instrument manipulators 73, more or fewer surgical instrument manipulators 73 may be used.

A functional teleoperated surgical system will generally include a vision system portion that enables a user of the teleoperated surgical system to view the surgical site from outside the patient's body 12. The vision system typically includes a camera instrument 26C for capturing video images and one or more video displays for displaying the captured video images. In some surgical system configurations, the camera instrument 26C includes optics that transfer the images from a distal end of the camera instrument 26C to one or more imaging sensors (e.g., CCD or CMOS sensors outside of the patient's body 12. Alternatively, the imaging sensor(s) can be positioned at the distal end of the camera instrument 26C, and the signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, Calif.

Referring to FIG. 5A, mounted to each surgical instrument manipulator 73 is a surgical instrument 26 that operates at a surgical site within the patient's body 12. Each surgical instrument manipulator 73 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 73 to move its associated surgical instrument around a center of motion on the instrument that stays stationary with reference to the patient, and this center of motion is typically located at the position where the instrument enters the body.

In one aspect, surgical instruments 26 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, such as one or more motors to which surgical instrument 26 is coupled. In this manner, the surgical instrument 26 moves in response to a medical person's movements of the control input. In one aspect, one or more control inputs are included in a surgeon's console such as surgeon's console 16 shown at FIG. 2. A surgeon can manipulate control inputs 36 of surgeon's console 16 to operate teleoperated actuators of patient-side cart 54. The forces generated by the teleoperated actuators are transferred via drivetrain mechanisms, which transmit the forces from the teleoperated actuators to the surgical instrument 26.

Referring to FIG. 5A, in one aspect, a surgical instrument 26 and a cannula 27 are removably coupled to manipulator 73, with the surgical instrument 26 inserted through the cannula 27. One or more teleoperated actuators of the manipulator 73 move the surgical instrument 26 as a whole. The manipulator 73 further includes an instrument carriage 75. The surgical instrument 26 is detachably connected to the instrument carriage 75. In one aspect, the instrument carriage 75 houses one or more teleoperated actuators inside that provide a number of controller motions that the surgical instrument 26 translates into a variety of movements of an end effector on the surgical instrument 26. Thus the teleoperated actuators in the instrument carriage 75 move only one or more components of the surgical instrument 26 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In an alternate embodiment, instrument carriage 75 does not house teleoperated actuators. Teleoperated actuators that enable the variety of movements of the end effector of the surgical instrument 26 are housed in a location remote from the instrument carriage 75, e.g., elsewhere on patient-side cart 54. A cable-based force transmission mechanism or the like is used to transfer the motions of each of the remotely located teleoperated actuators to a corresponding instrument-interfacing actuator output located on instrument carriage 75. In some embodiments, the surgical instrument 26 is mechanically coupled to a first actuator, which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing or a jaws end effector.

Figure 5B:
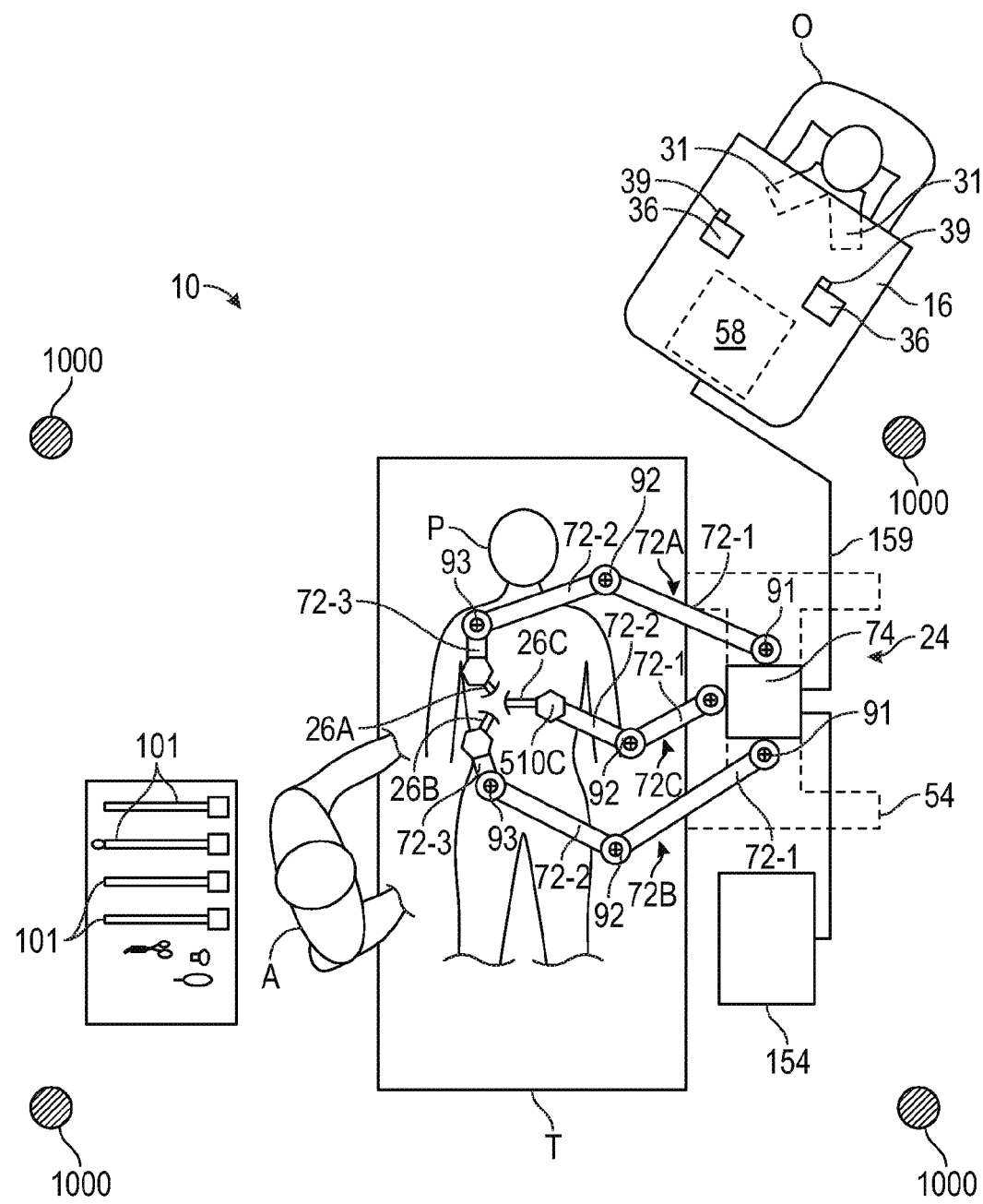
FIG. 5B is an illustrative simplified block diagram showing an example positioning of mechanical support arms of the teleoperation surgery system during a surgical procedure in accordance with some embodiments.

FIG. 5B is an illustrative simplified block diagram showing an example positioning of mechanical support arms 72A-72C of the teleoperation surgery system 10 during a surgical procedure in accordance with some embodiments. In some embodiments, the patient-side system 54 includes at least three mechanical support arms 72A-72C. In some embodiments, each of the mechanical support arms 72A-72C includes rotatably mounted first, second and third segments 72-1, 72-2 and 72-3. A center-located mechanical support arm 72 may support an endoscopic camera 26C suitable for capture of images within a field of view of the camera. The mechanical support arms 72 to the left and right of center may support instruments 26A and 26B, respectively, which may manipulate anatomical tissue. During setup for a surgical procedure, the support arm segments are pre-positioned to support endoscope and instruments in precise position and orientation to for robot assisted manipulation by a surgeon to perform a medical procedure.

A user or operator O (generally a surgeon) performs a surgical procedure on patient P by manipulating control input devices 36, such as hand grips and foot pedals at a master control console 16. The operator can view video frames of images of a surgical site inside a patient's body through a stereo display viewer 31. A computer processor 58 of the console 16 directs movement of teleoperationally controlled endoscopic surgical instruments 26A-26C via control lines 159, effecting movement of the instruments using a patient-side system 24 (also referred to as a patient-side cart).

Figure 5C:
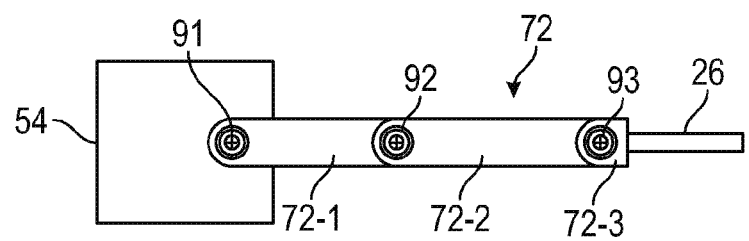
FIGS. 5C-5E are illustrative drawings representing a segmented mechanical support arm with its first, second and third segments and in three different horizontal positions in accordance with some embodiments.
Figure 5D:
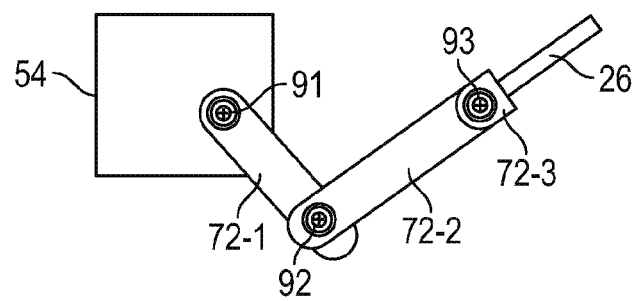
Figure 5E:
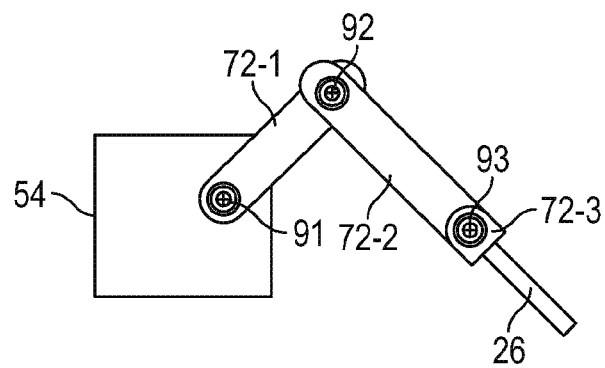

FIGS. 5C-5E are illustrative drawings representing a segmented mechanical support arm 72 with its first, second and third segments 72-1, 72-2 and 72-3 in three different horizontal positions in accordance with some embodiments. In order to simplify the explanation, only one mechanical support arm is shown although the surgical system includes multiple support arms as represented in FIG. 1. The first segment 72-1 incudes a first end portion 81-1 and a second end portion 81-2. The second segment 72-2 incudes a first end portion 82-1 and a second end portion 82-2. The third segment 72-3 incudes a first end portion 83-1 and a second end portion 83-2.

The first segment 72-1 is rotatably mounted at its first end portion 81-1 for horizontal rotation about a respective vertical axis 91 at the vertical support structure 74. The second segment 72-2 is rotatably mounted at its first end portion 82-1 for horizontal rotation about a respective vertical axis 92 at the second end portion 81-2 of the corresponding first segment 72-1. The third segment 72-3 is mounted at its first end portion 83-1 for horizontal rotation about a respective vertical axis 93 at the second end portion 82-2 of its corresponding second segment 72-2.

FIG. 5C is an illustrative drawing showing the three segments of the segmented mechanical support arm 72 in fully extended to the right (from the drawing perspective). FIG. 5D is an illustrative drawing showing the first segment 72-1 rotated clockwise about the vertical axis 91 and the second segment 72-2 rotated counter-clockwise about the vertical axis 92 relative to their positions in FIG. 5C, and with the rotational position of the third segment 72-3 unchanged relative to the second segment 72-2. FIG. 5E is an illustrative drawing showing the first segment 72-1 rotated counter-clockwise about the vertical axis 91 and the second segment 72-2 rotated clockwise about the vertical axis 92 relative to their positions in FIG. 5A, and with the rotational position of the third segment 72-3 unchanged relative to the second segment 72-2.

Figure 5F:
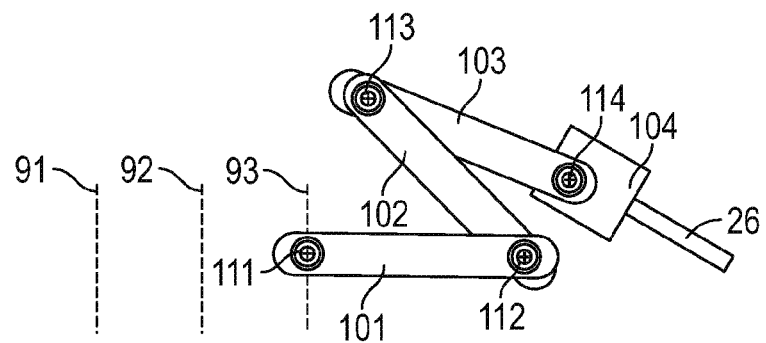
FIGS. 5F-5G are illustrative drawings representing certain details of the third segment of FIGS. 5C-5E and showing the third segment in two different vertical positions in accordance with some embodiments.
Figure 5G:
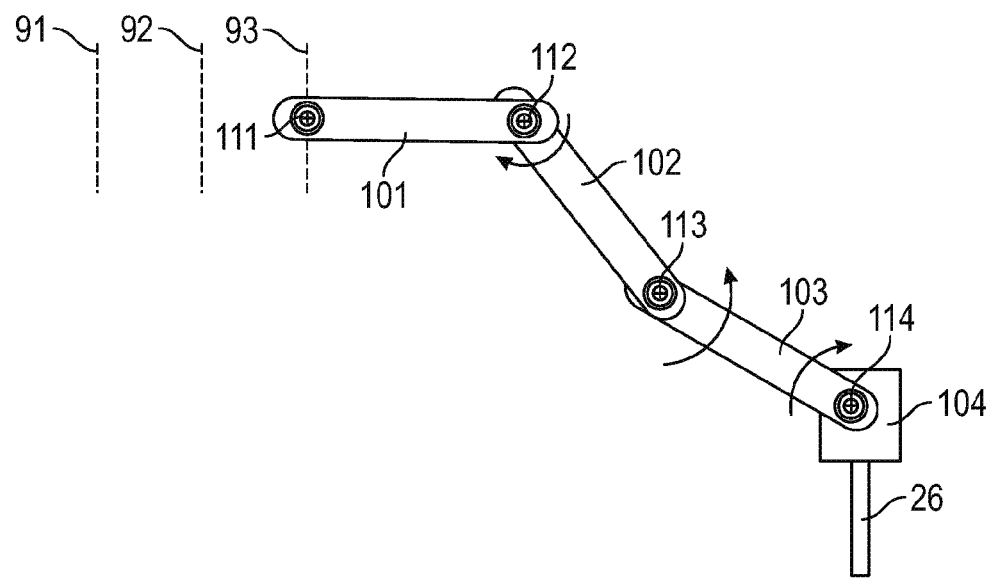

FIGS. 5F-5G are illustrative drawings representing certain details of the third segment 72-3 of FIGS. 5C-5E and showing the third segment 72-3, also referred to as an instrument manipulator, in two different vertical positions in accordance with some embodiments. The third mechanical support arm segment 72-3 includes first, second, third and fourth sub-segments 101-104.

The first sub-segment 101 incudes a first end portion 101-1 and a second end portion 101-2. The second sub-segment 102 incudes a first end portion 102-1 and a second end portion 102-2. The third sub-segment 103 incudes a first end portion 103-1 and a second end portion 103-2. The fourth sub-segment 104 incudes a first end portion 104-1 and a second end portion 104-2.

The first sub-segment 101 is rotatably mounted at its first end portion 101-1 for vertical rotation about a respective horizontal axis 111 at the second end portion 82-2 of the second segment 72-2. The second sub-segment 102 is rotatably mounted at its first end portion 102-1 for vertical rotation about a respective horizontal axis 112 at the second end portion 101-2 of the first sub-segment 101. The third sub-segment 103 is rotatably mounted at its first end portion 103-1 for vertical rotation about a respective horizontal axis 113 at the second end portion 102-2 of the second sub-segment 102. The fourth sub-segment 104 is rotatably mounted at its first end portion 104-1 for vertical rotation about a respective horizontal axis 114 at the second end portion 103-2 of the third sub-segment 103. In accordance with some embodiment, the fourth sub-segment 104 includes a mount structure 120 to securely mount a surgical instrument during a surgical procedure.

FIG. 5F is an illustrative drawing showing the four sub-segments of the third mechanical support arm segment 72-3 in substantially folded or contracted configuration position in accordance with some embodiments. FIG. 5G is an illustrative drawing showing the four sub-segments of the third mechanical support arm segment 72-3 in a partially configuration position in accordance with some embodiments. More specifically, in FIG. 5G, the rotational position of the first sub-segment 101 about horizontal axis 111 is unchanged relative to its rotation position in FIG. 5F. The second sub-segment 102 is rotated clockwise about horizontal axis 112 relative to its rotation position in FIG. 5F. The third sub-segment 103 is rotated counter-clockwise about horizontal axis 113 relative to its rotation position in FIG.

5F. The fourth sub-segment 104 is rotated clockwise about horizontal axis 114 relative to its rotation position in FIG. 5F.

Figure 6:
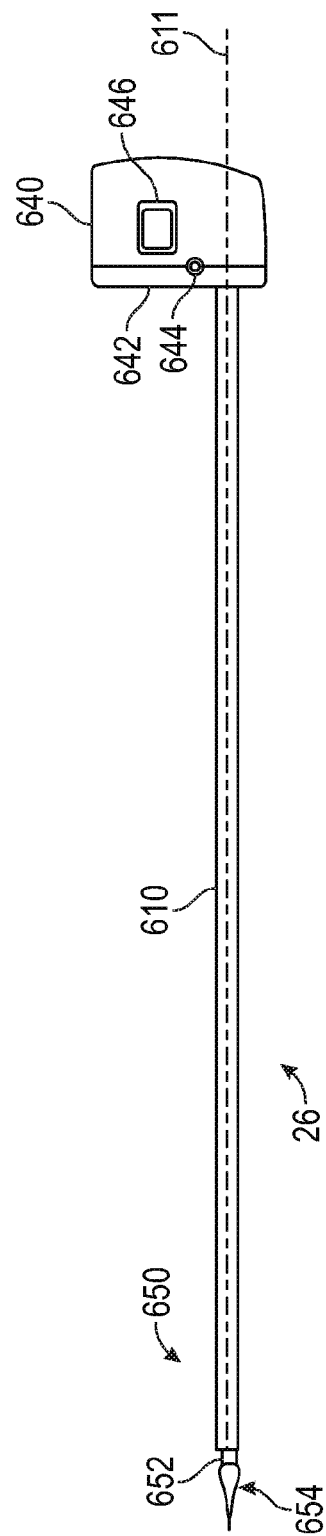
FIG. 6 is an elevation view of a surgical instrument.

FIG. 6 is a side view of a surgical instrument 26, which includes a distal portion 650 and a proximal control mechanism 640 coupled by an elongate tube 610 having an elongate tube centerline axis 611. The surgical instrument 26 is configured to be inserted into a patients body and is used to carry out surgical or diagnostic procedures. The distal portion 650 of the surgical instrument 26 can provide any of a variety of end effectors 654, such as the forceps shown, a needle driver, a cautery device, a cutting tool, an imaging device (e.g., an endoscope or ultrasound probe), or the like. The surgical end effector 654 can include a functional mechanical degree of freedom, such as jaws that open or close, or a knife that translates along a path. In the embodiment shown, the end effector 654 is coupled to the elongate tube 610 by a wrist 652 that allows the end effector to be oriented relative to the elongate tube centerline axis 611. Surgical instrument 26 can also contain stored (e.g., on a semiconductor memory associated with the instrument) information, which may be permanent or may be updatable by a surgical system configured to operate the surgical instrument 26. Accordingly, the surgical system may provide for either one-way or two-way information communication between the surgical instrument 26 and one or more components of the surgical system.

Figure 7:
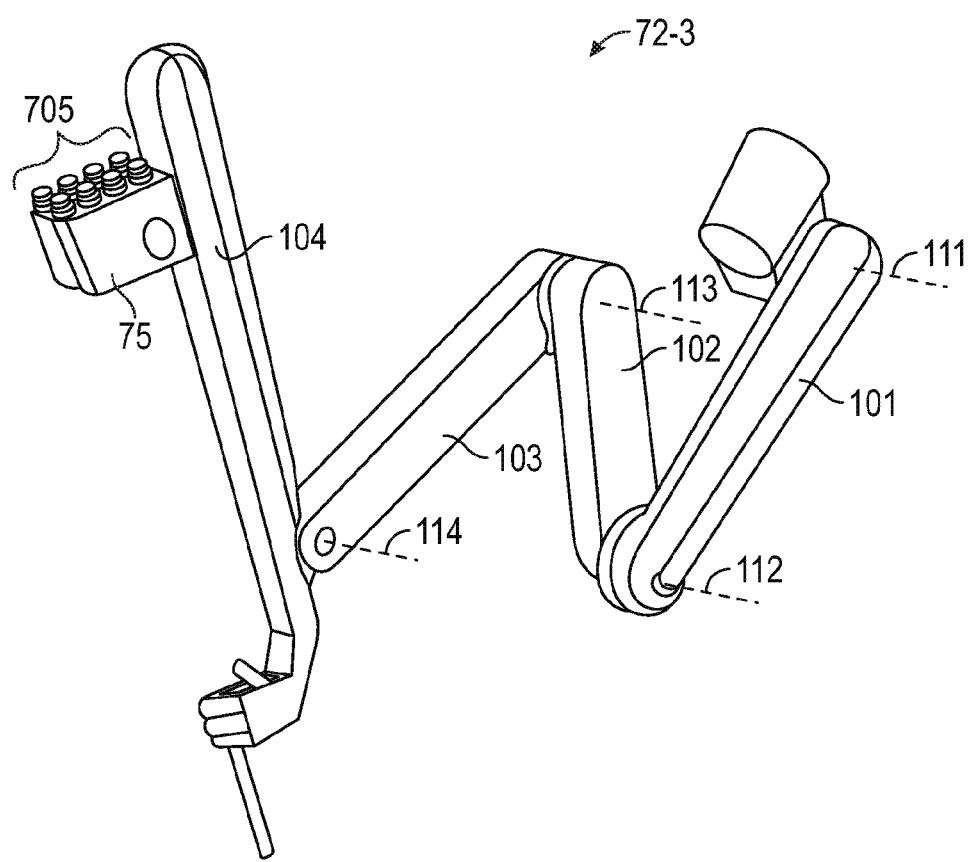
FIG. 7 is a perspective view of an instrument manipulator.

FIG. 7 is a perspective view of a third arm segment 72-3, also referred to as a surgical instrument manipulator in accordance with some embodiments. The third arm segment 72-3 is shown with no surgical instrument installed. The third arm segment 72-3 includes first, second, third and fourth sub-segments 101-104 rotatably mounted about horizontal axes 111-114 as shown and as described above with reference to FIGS. 5F-5G. The third arm segment 72-3 further includes an instrument carriage 75 to which a surgical instrument (e.g., surgical instrument 26) can be detachably connected. Instrument carriage 75 houses a plurality of teleoperated actuators. Each teleoperated actuator includes an actuator output 705. When a surgical instrument is installed onto instrument manipulator 72-3, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs 705 directly contacting corresponding instrument inputs. In another aspect, this mechanical coupling occurs through an intermediate interface, such as a component of a drape configured to provide a sterile barrier between the third segment/instrument manipulator 72-3 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 72-3 is surgical instrument 26, shown at FIG. 6. Referring to FIG. 6, in one aspect, movement of one or more instrument inputs of proximal control mechanism 640 by corresponding teleoperated actuators rotates elongate tube 610 (and the attached wrist 652 and end effector 654) relative to the proximal control mechanism 640 about elongate tube centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.). Accordingly, various mechanical degrees of freedom of a surgical instrument installed onto an instrument manipulator 26 can be moved by operation of the teleoperated actuators of instrument carriage 75.

Annotating a Recorded Video

Figure 8:
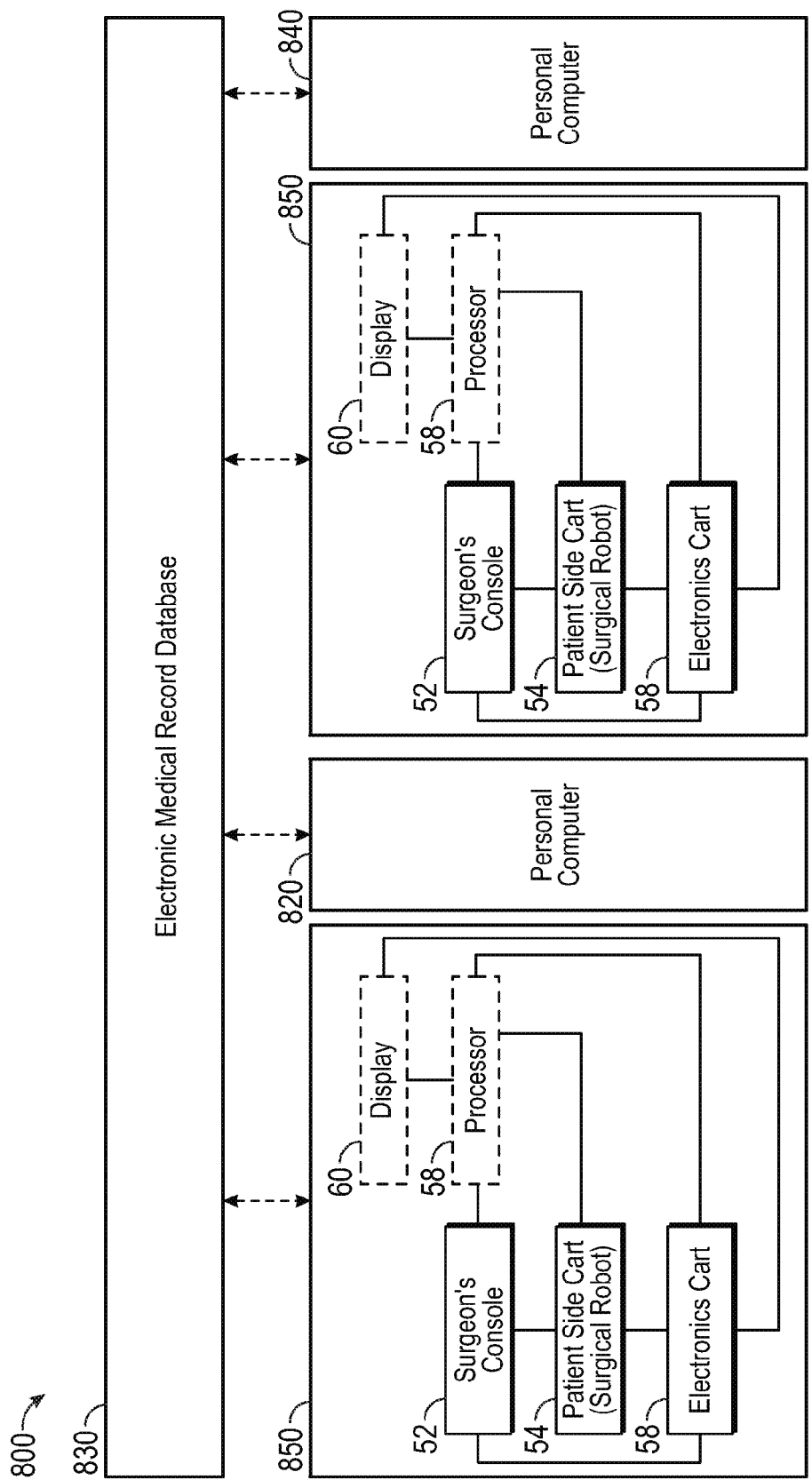
FIG. 8 is a diagrammatic illustration of a surgical planning tool.

FIG. 8 shows a schematic diagram of an exemplary surgical planning tool 800. In one aspect, surgical planning tool 800 includes a teleoperated surgical system 850 in data communication with an electronic medical device record database 830. Teleoperated surgical system 850 shown here is similar to teleoperated surgical system 850 shown at FIG. 4. In one aspect, electronic medical record database 830 includes the medical records of patients that have undergone treatment at a particular hospital. Database 830 can be implemented on a server located on-site at the hospital. The medical record entries contained in the database 830 can be accessed from hospital computers through an intranet network. Alternatively, database 830 can be implemented on a remote server located off-site from the hospital, e.g., using one of a number of cloud data storage services. In this case, medical record entries of database 830 are stored on the cloud server, and can be accessed by a computer with interact access.

In one aspect, a surgical procedure is performed on a first patient using teleoperated surgical system 850. An imaging device associated with teleoperated surgical system 850 captures images of the surgical site and displays the captured images as frames of a video on a display of surgeon's console 52. In one aspect, a medical person at surgeon's console 52 highlights or annotates certain patient anatomy shown in the displayed video using an input device of surgeon's console 52. An example of such an input device is control input 36 shown at FIG. 2, which is coupled to a cursor that operates in conjunction with a graphic user interface overlaid onto the displayed video. The graphic user interface can include a QWERTY keyboard, a pointing device such as a mouse and an interactive screen display, a touch-screen display, or other means for data or text entry. Accordingly, the medical person can highlight certain tissue of interest in the displayed image or enter a text annotation.

In one aspect, the surgical site video is additionally displayed on a display located on electronics cart 56. In one aspect, the display of electronics cart is a touch-screen user interface usable by a medical person to highlight and annotate certain portions of patient anatomy shown on an image that is displayed for viewing on the display on the electronics cart. A user, by touching portions of patient anatomy displayed on the touch-screen user interface, can highlight portions of the displayed image. Additionally, a graphic interface including a QWERTY keyboard can be overlaid on the displayed image. A user can use the QWERTY keyboard to enter text annotations.

In one aspect, the surgical site video captured by the imaging device associated with teleoperated surgical system 850 is recorded by the teleoperated surgical system 850, and stored on database 830, in addition to being displayed in real time or near real time to a user. Highlights and/or annotations associated with the recorded video that were made by the user can also be stored on database 830. In one aspect, the highlights made by the user are embedded with the recorded video prior to its storage on database 830. At a later time, the recorded video can be retrieved for viewing. In one aspect, a viewer of the recorded video can select whether the highlights are displayed or suppressed from view. Similarly, annotations associated with the recorded video can also be stored on database 830. In one aspect, the annotations made by the user are used to tag the recorded video, and can be used to provide as a means of identifying the subject matter contained in the recorded video. For example, one annotation may describe conditions of a certain disease state. This annotation is used to tag the recorded video. At a later time, a person desiring to view recorded procedures concerning this disease state can locate the video using a key word search.

Retrieval of Stored Video

In some cases, it is desirable for a medical person to be able to view video recordings of past surgical procedures performed on a given patient. In one aspect, a patient who previously underwent a first surgical procedure to treat a medical condition subsequently requires a second surgical procedure to treat recurrence of the same medical condition or to treat anatomy located nearby to the surgical site of the first surgical procedure. In one aspect, the surgical site events of the first surgical procedure were captured in a surgical site video recording, and the video recording was archived in database 830 as part of the patient's electronic medical records. Prior to performing the second surgical procedure on the patient, a medical person can perform a search of database 830 to locate the video recording of the patient's earlier surgical procedure.

In some cases, it is desirable for a medical person planning to perform a surgical procedure on a patient to be able to view video recordings of similar surgical procedures performed on persons having certain characteristics similar to the patient. In one aspect, surgical site video recordings of surgical procedures can be tagged with metadata information such as the patient's age, gender, body mass index, genetic information, type of procedure the patient underwent, etc., before each video recording is archived in database 830. In one aspect, the metadata information used to tag a video recording is automatically retrieved from a patient's then-existing medical records, and then used to tag the video recording before the video recording is archived in database 830. Accordingly, prior to performing a medical procedure on a patient, a medical person can search database 830 for video recordings of similar procedures performed on patients sharing certain characteristics in common with the patient. For example, if the medical person is planning to use teleoperated surgical system 850 to perform a prostatectomy on a 65 year-old male patient with an elevated body mass index using, the medical person can search database 830 for surgical site video recordings of prostatectomies performed using teleoperated surgical system 850 on other males of similar age and having similarly elevated body mass index.

In one aspect, a video recording of a surgical procedure is communicated by database 830 to an optional personal computer 820 (as indicated by dashed line), and made available for viewing by a medical person who plans to perform a surgical procedure. Additionally or in the alternative, the video recording of the earlier surgical procedure can be communicated by database 830 to teleoperated surgical system 850, and made available for viewing preoperatively or intraoperatively. In one aspect, the video recording is displayed by teleoperated surgical system 850 on a display located on surgeon's console 52. In another aspect, the video recording of the first surgical procedure is displayed on a display located on electronics cart 56.

Cloud-Based Video Database

In one aspect, database 830 is implemented on a remote server using a cloud data storage service and is accessible by multiple health care providers. Referring to FIG. 8, as shown by dashed line, surgical planning tool 800 optionally includes teleoperated surgical system 850 (as indicated by dashed line) and personal computer 840 (as indicated by dashed line). In one aspect, teleoperated surgical system 850 is similar to teleoperated surgical system 850 and personal computer 840 is similar to personal computer 820, except that teleoperated surgical system 850 and personal computer 820 are located at a first health care provider and teleoperated surgical system 850 and personal computer 840 are located at a second health care provider. In one aspect, a first patient requires surgical treatment of a medical condition, and undergoes a surgical procedure using teleoperated surgical system 850 at the first health care provider. A video recording of the surgical procedure is archived on database 830. At a later time, a second patient requires surgical treatment of the same medical condition, and plans to receive surgical treatment using teleoperated surgical system 850 at the second health care provider. Prior to performing the surgical procedure on the second patient, a medical person accesses database 830 through a secure internet connection and searches database 830 for surgical site video recordings of similar procedures. In one aspect, the medical person treating the second patient is able to retrieve from database 830 the video recording of first patient's surgical procedure, without acquiring knowledge of the identity of the first patient. In this manner, the privacy of the first patient is maintained. In one aspect, the video recording of the first patient's surgical procedure includes highlights and/or annotations made by the medical person who treated the first patient.

Computer Based Pattern Matching and Analysis

Surgical planning tool 800 can includes a pattern matching and analysis algorithm implemented in the form of computer executable code. In one aspect, the pattern matching and analysis algorithm is stored in a non-volatile memory device of surgical planning tool 800, and is configured to analyze the video recordings archived in database 830. As discussed previously, each of the video recordings archived in database 830 can be tagged and/or embedded with certain metadata information. This metadata information can include patient information such as patient age, gender, and other information describing the patient's health or medical history. Additionally, as discussed previously, the metadata information can include highlights or annotations made by a medical person. In one aspect, these highlights and annotations are embedded with the video recording and archived together with the video in database 830.

In one aspect, pattern matching and analysis algorithm includes an image analysis component that identifies patterns in shapes and colors that are shared amongst multiple video recordings stored on database 830. The pattern matching and analysis algorithm then reviews the tagged metadata associated with this subset of video recordings to determine whether any words or phrases are frequently associated with videos within this subset. These analyses performed by pattern matching and analysis algorithm can be used to assist medical persons in making determinations about patient anatomy, preferred surgical approaches, disease states, potential complications, etc.

A Method of Using a Surgical Planning Tool

Figure 9:
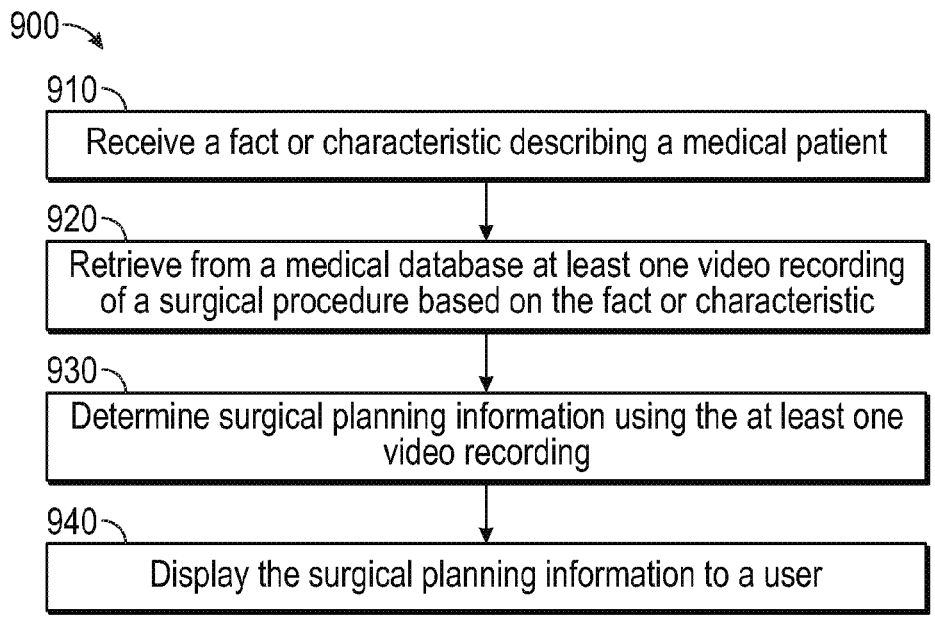
FIG. 9 is a flow diagram of a method of using a surgical planning tool.

FIG. 9 shows a method 900 of using a surgical planning tool. In one aspect, the surgical planning tool is similar to surgical planning tool 800 at FIG. 8. At 910, a fact or characteristic describing a medical patient, e.g., a medical condition suffered by a patient, is received by a medical device. Medical device can receive this fact or circumstance via a user interface located on a teleoperated surgical system (e.g., teleoperated surgical system 10 at FIG. 1 or teleoperated surgical system 50 at FIG. 4), or alternatively, through a personal computer similar to personal computer 820 at FIG. 2. At 920, the medical device uses the fact or characteristic received at 910 to retrieve at least one relevant video recording of a surgical procedure from a medical device database. At 930, the medical device uses the video recordings to determine surgical planning information. In one aspect, the surgical planning information includes the types of instruments used in the recorded procedure. At 940, the medical device displays to a user the surgical planning information determined at 930.

Mechanical Support Arm Positioning and Surgical System Module Positioning

It will be appreciated that positioning of mechanical surgical arms 72 including positioning of their multiple sub-segments 72-1, 72-2, 72-3, during a surgical procedure may depend upon a variety of factors such as the type of surgical procedure, patient anatomical features, patient body position, operating room layout for example. Different surgeries may involve different surgical incision patterns. Different patient anatomies may result in different spacings between incisions used in a surgical procedure. Different patients may require different body positions or orientations relative to an operating room table during a surgery. Different operating room layouts may require repositioning of the mechanical surgical arms to accommodate for the physical limitations introduced by the OR layout.

Figure 10A:
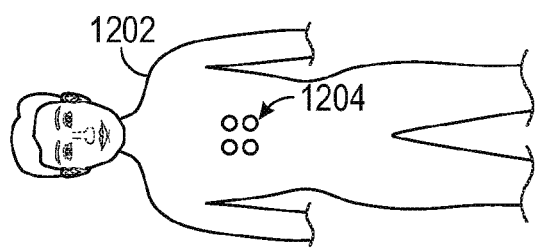
FIGS. 10A-10B are illustrative top elevation views of two example patients with different anatomical dimensions having similar incision pattern suited to the same surgical procedure but having different spacing between incisions due to the different anatomical spacing.
Figure 10B:
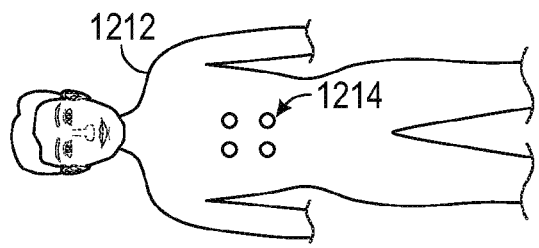

FIGS. 10A-10B are illustrative top elevation views of two example patients 1202, 1206 with different anatomical dimensions having similar incision patterns suited to the same first surgical procedure but having different spacing between incisions due to the different anatomical spacing. FIG. 10A is an illustrative drawing representing a first patient 1202 having smaller anatomical dimensions having first surgical incisions 1204 in a first pattern with first spacing. FIG. 10B is an illustrative drawing representing a second patient 1206 having larger anatomical dimensions and having second incisions 1208 in the first pattern with second spacing. It will be appreciated that the pattern of the first incisions 1204 in the first patient 1202 and of the second incisions 1208 in the second patient 1206 are similar, since each patient undergoes the same surgery. However, spacing between first incisions 1204 in the first patient 1202 and the second incisions 1208 in the second patient 1206 is different due to the different anatomical dimensions of the two patients. It will be appreciated that each of the multiple mechanical support arms 72 of FIGS. 5A-5G including each of its multiple sub-segments 72-1, 72-2, 72-3 is set up in a different position to dispose instruments 26 for insertion into the first incisions 1204 in the first patient 1202 and to insert instruments 26 in the second incisions in the second patient. The mechanical support arm set up information is recorded using processor 58, for example, in a computer readable storage device as explained more fully below.

Figure 11A:
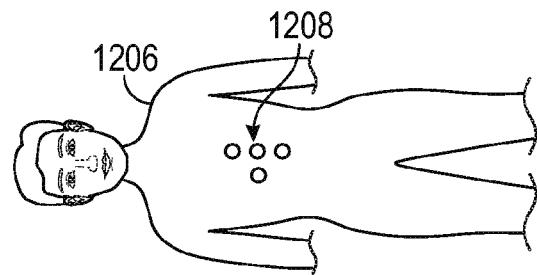
FIGS. 11A-11B are illustrative top elevation views of two different example patients that have different anatomical dimensions from each other and that have similar incision patterns suited to the same second surgical procedure.
Figure 11B:
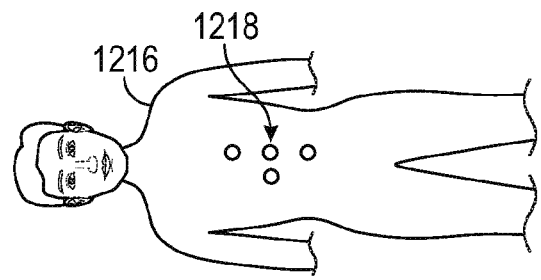

FIGS. 11A-11B are illustrative top elevation views of two different example patients 1212, 1216 that have different anatomical dimensions from each other and that have similar incision patterns 1214, 1218 suited to the same second surgical procedure. The third and fourth patients 1212, 1216 have different spacing between their incisions due to the different anatomical spacing due to different body dimensions. It can be seen that the incision patterns for the second surgical procedure represented in FIG. 11A are different from those of the first surgical procedure represented in FIGS. 10A-10B. It will be appreciated that the positions of the multiple mechanical support arms 72 of FIGS. 5A-5G will be different for the second surgical procedure than they will be for the first surgical procedure. The mechanical support arm set up information is recorded using processor 58, for example, in a computer readable storage device as explained more fully below.

Figure 12A:
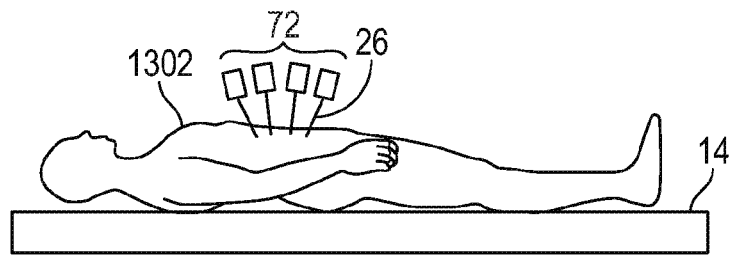
FIGS. 12A-12B are illustrative side views of two example patients incisions who are disposed on an operating room table at different tilt angle positions who are subjected to the same surgical procedure and have the same types of surgical instrument inserted within surgical incisions.
Figure 12B:
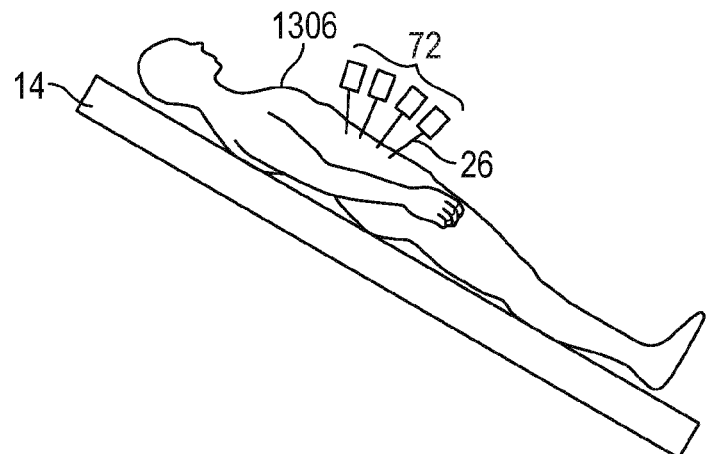

FIGS. 12A-12B are illustrative side views of two example patients 1302, 1306 who are disposed on an operating room table 14 at different tilt angle positions who are subjected to the same surgical procedure and have the same types of surgical instrument inserted within surgical incisions. FIG. 12A is an illustrative drawing showing the example first patient 1302 lying on a surgical table 14 that is aligned parallel to the ground so that head, abdomen and legs are level. Four surgical instruments are inserted within surgical incisions in the first patient's body for use in the surgical procedure. FIG. 12B is an illustrative drawing showing the example second patient 1306 lying on a surgical table 14 that is tilted at an angle so that the head is raised higher and the legs are lower. Four surgical instruments are inserted within surgical incisions in the second patient's bod for use in the surgical procedure. It will be appreciated that each of the multiple mechanical support arms 72 of FIGS. 5A-5G including each of its multiple sub-segments 72-1, 72-2, 72-3 is set up in a different position to dispose instruments 26 for insertion into incisions in the first patient 1202 and to insert instruments 26 into incisions in the second patient 1204. It will be appreciated that a scope with different angle might be used, for example a straight 0-degrees scope for first patient 1302 and a down-looking 30-degree scope for second patient 1306; In such case kinematics of the arms 72 might be used to re-adjust the arm configuration for the patient 1306 corresponding to the endoscope configuration. The mechanical support arm set up information is recorded using processor 58, for example, in a computer readable storage device as explained more fully below.

It will be appreciated that positioning of surgical system modules such as including positioning of master control console 16, surgical instrument tray 30, electronics cart 24 and patient side cart 54 may depend upon a variety of factors such as the type of surgical procedure, operating room layout and operating room personnel movement patterns during the surgery, for example. Different operating room layouts may require different system module positioning due to different fixtures within the operating room. Different surgery room personnel movement patterns may require different system module positioning in to facilitate efficient and safe movement of personnel during the surgical procedure, for example.

Figure 13A:
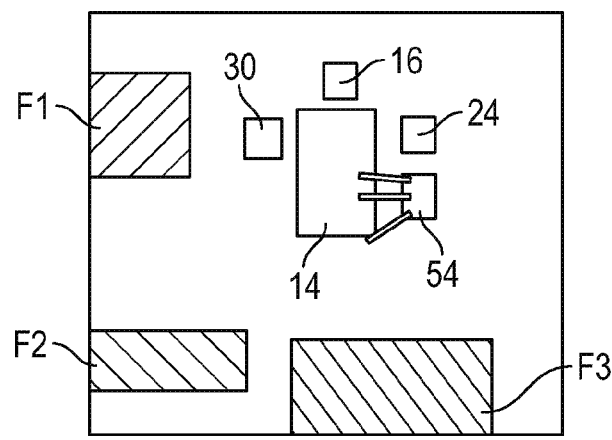
FIGS. 13A-13C are illustrative drawings representing three different surgical system module dispositions.
Figure 13B:
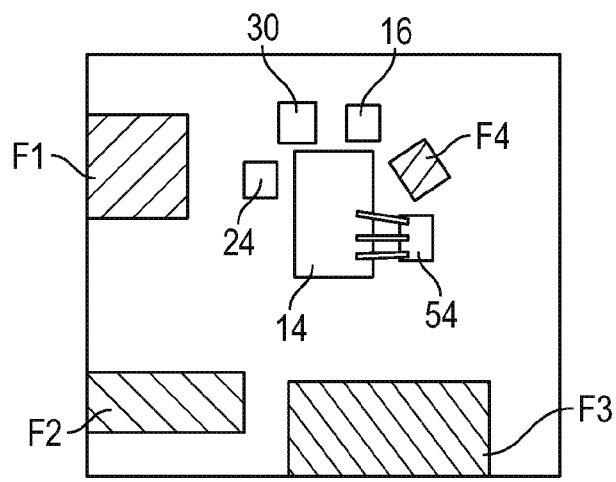
Figure 13C:
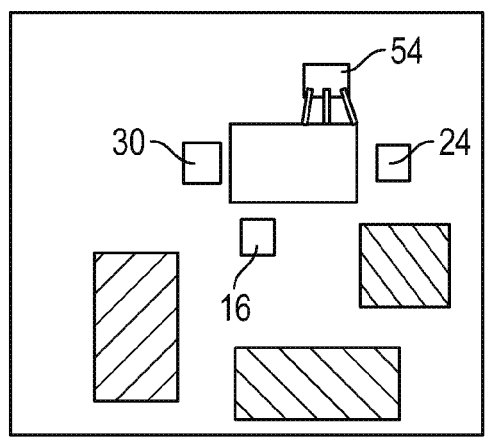

FIGS. 13A-13C are illustrative drawings representing three different surgical system module dispositions. FIG. 13A is illustrative drawings in which an operating room contains fixtures F1-F3 laid out as shown in which surgical system modules 16, 30, 24 and 54 are positioned in a first disposition as shown. The fixtures may include structures such as poles, cabinets or walls or obstacles such as electrical outlets, for example. FIG. 13B is illustrative drawings in which an operating room contains fixtures F1-F3 laid out in FIG. 13A and that also includes fixture F4 laid out as shown in which surgical system modules 16, 30, 24 and 54 are positioned in a second disposition as shown. FIG. 13C is illustrative drawings in which an operating room contains fixtures F5-F7 laid out as shown in which surgical system modules 16, 30, 24 and 54 are positioned in a third disposition as shown.

Referring again to FIGS. 5A-5B, there are shown position sensors 1000 to sense position of objects within an operating room in accordance with some embodiments. During a surgery, the position sensors 1000 sense patient position, operating room fixture positions, system module positions and operating room personnel positions. FIGS. 5A-5B show position sensors 1000 disposed at four corners at a height to have a line of sight to the patient. Only two of the four sensors 1000 are visible in FIG. 5B. The position sensors produce information indicative of positions of patient anatomy features such as body surface, patient skeleton pose on the operating room table and relative pose of surgical system with respect to patient anatomy. In some embodiments, the position sensors include laser scan sensors that scan an operating room and its contents to determine positions of items within the room. In some embodiments, the position sensors 1000 include infrared (IR) scan sensors. Information indicating the sensed patient position information, operating room layout and system module positions is recorded, using processor 58 for example, in a computer readable storage device as explained more fully below. In some embodiments, operating personnel are equipped with RFID tags that can be tracked to identify personnel within the operating room.

Figure 14:
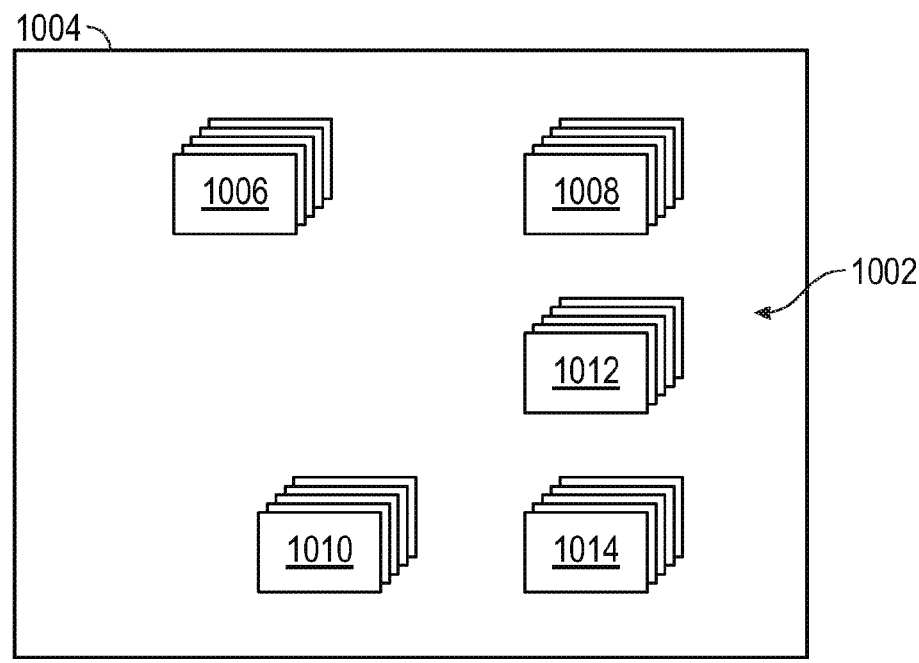
FIG. 14 is an illustrative drawing representing storage atlas in a computer readable storage device in accordance with some embodiments.
Figure 15:
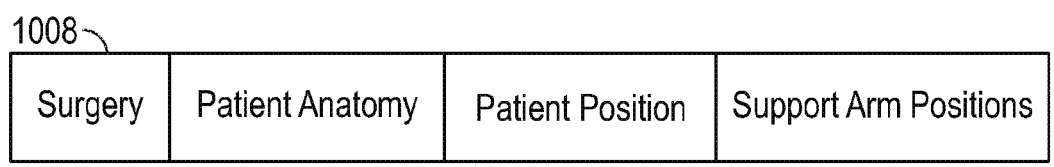
FIG. 15 is an illustrative drawing representing an example instance of the second information structure included within the atlas in accordance with some embodiments.
Figure 16:
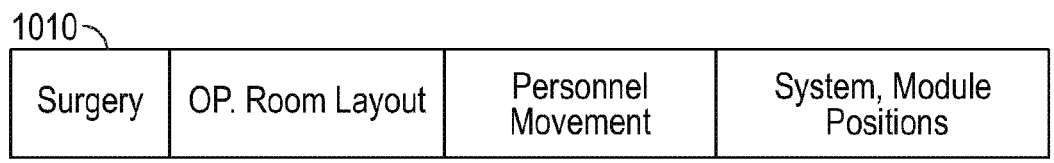
FIG. 16 is an illustrative drawing representing an example instance of the third information structure included within the atlas in accordance with some embodiments.

FIG. 14 is an illustrative drawing representing storage atlas 1002 in a computer readable storage device 1004 in accordance with some embodiments. The storage atlas 1002 includes first information structures 1006 that indicate instances of previously performed surgical procedures. Second information structures 1008 associate surgical procedures with patient anatomical features and with patient disposition on an operating room table and with mechanical support arm position during the surgical procedure. Third information structures 1010 associate surgical procedures with operating room layout features and with operating room personnel movement patterns during the surgical procedures and with surgical system module positions during the surgical procedures. First rules information structures 1012 associate patient anatomical feature information and patient position information with mechanical set up control signals, Second rules information structures 1014 associate operating room layout information and operating room personnel information with system module position information. FIG. 15 is an illustrative drawing representing an example instance of the second information structure 1008 included within the atlas 1002 in accordance with some embodiments. FIG. 16 is an illustrative drawing representing an example instance of the third information structure 1010 included within the atlas 1002 in accordance with some embodiments.

Figure 17:
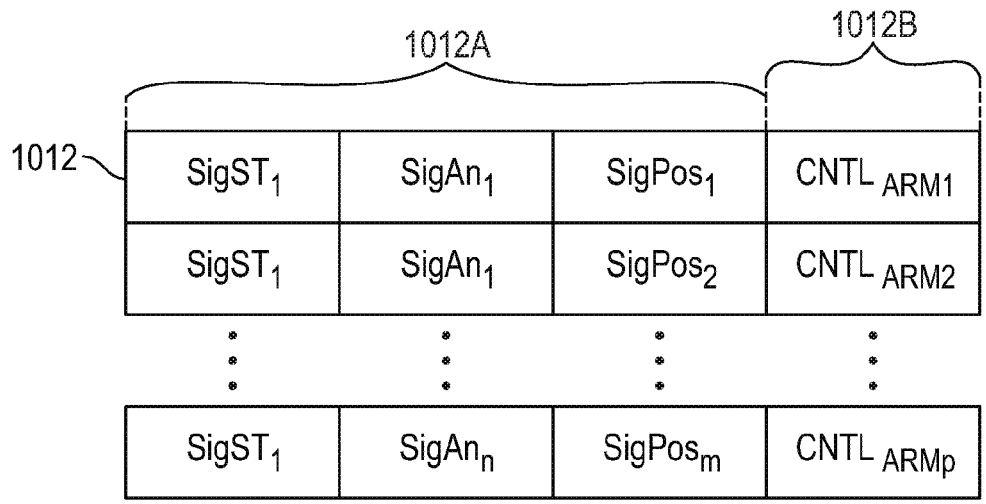
FIG. 17 is an illustrative drawing representing an example first control signal rules information structure to associate patient anatomical feature information and patient position information with mechanical support arm position control signals, in accordance with some embodiments.

FIG. 17 is an illustrative drawing representing an example first rules information structure 1012 to associate patient anatomical feature information and patient position information with mechanical support arm position control signals, in accordance with some embodiments. The first rules are developed based upon data from prior surgeries represented in the first and second data information structures 1006, 1008. The first rules correlate patterns of patient anatomy and patient position with control signals used to control set up of positions of the mechanical support arms 76 for use during a first type of surgical procedure.

More particularly, for an example first type of surgical procedure, the first rules information structure 1012 associates surgical procedure signatures ($SigST_1$ ... $SigST_l$) patient anatomy signatures ($SigAn_1$ ... $SigAn_n$) and patient position ($SigPos_1$ ... $SigPos_m$) signatures with mechanical arm position control signals ($CNTL_{ARM1}$ ... $CNTL_{ARMP}$). In some embodiments, a patient anatomy signature includes a multi-dimensional vector. In some embodiments, a patient anatomy signature indicates patient health record information such as body mass, height, age, demographic information and preoperative three dimensional images of the patient such as computed tomography (CT), Magnetic Resonance Imaging (MRI). In addition, a patient anatomy signature can include surgical planning information such as surface scans of patient body using structured light imaging systems or other depth sensing technologies such as time of flight and radiofrequency imaging, and geometric or physics-based models generated from the above information which can be used to estimate deformations of the patient body in given configurations. In some embodiments, patient position signature includes a multi-dimensional vector. In some embodiments, scanned patient position information is used to determine patient position information such as insufflation pressure, measurements from a pressure mat on the operating room table, three dimensional model of the patient body on the operating room table acquired by intraoperative imaging techniques including cone-beam CT, intraoperative CT or MRI, surface scanning techniques or multiple view surface reconstruction from a plurality of cameras. In accordance with some embodiments, different mechanical arm position control signals are associated with different combinations of patient anatomy signatures and patient position signatures. Patient position information acts as coarse information that indicates where a patient's body is located within an operating room. Patient anatomy information acts as fine information that indicate position of particular anatomical features of the patient's body.

In accordance with some embodiments, machine learning techniques can be used to generate first rules corresponding to patient anatomical feature signatures and to patient position signatures. More specifically, for example, classifiers can be used together with expert knowledge to correlate patient anatomical feature signatures and patient position signatures with mechanical arm position control signals. Surgical data within the first and second data information structures 1006, 1008 are evaluated, based upon expert surgeon input for example, to determine appropriate positions of mechanical arms 72 including positions of each of their segments 72-1, 72-2 and 72-3 and positions of each of their sub-segments 101-104. Control signals to effect the determined mechanical arm set up positions are associated in the first rules information structure 1012 with patient anatomical feature signatures and patient position signatures. In accordance with some embodiments, patient anatomical feature signatures and patient position signatures can be combined together to produce a combined signature that corresponds to a control signal.

Figure 18:
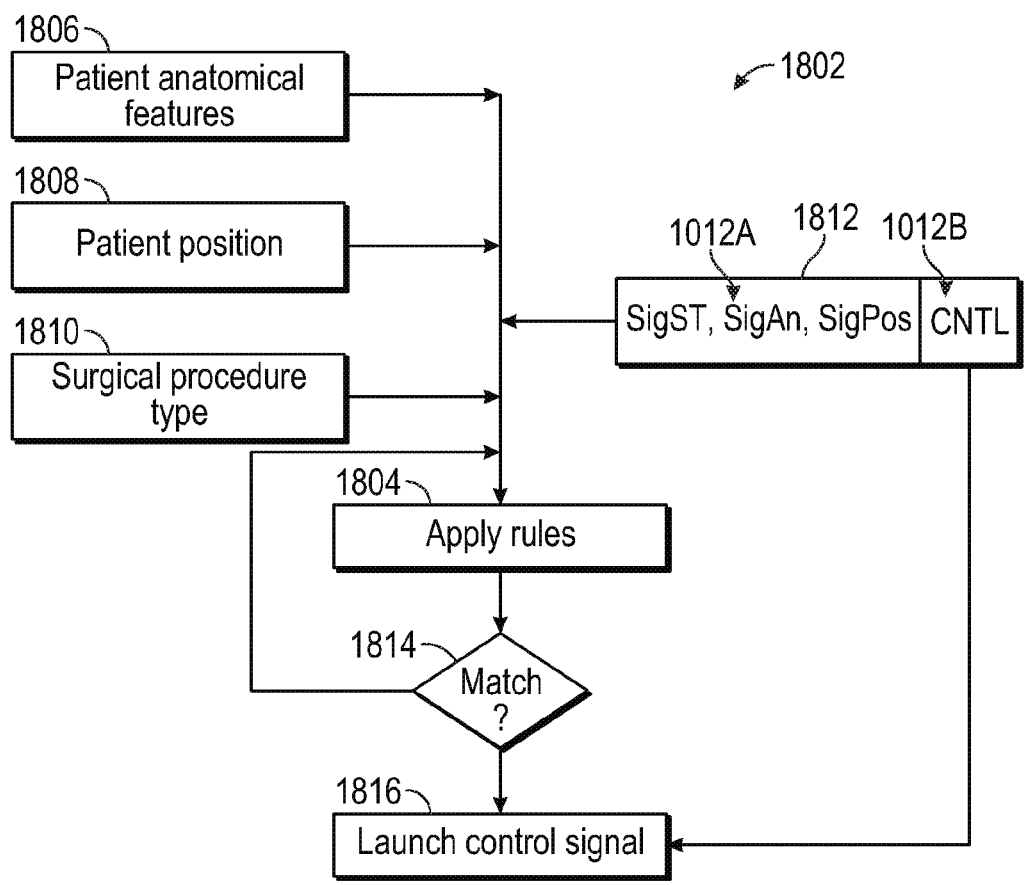
FIG. 18 is an illustrative flow diagram representing a process to produce a control signal based at least in part upon patient anatomical information, patient position information and surgical procedure type, in accordance with some embodiments.

FIG. 18 is an illustrative flow diagram representing a process 1802 to produce a control signal based at least in part upon patient anatomical information, patient position information and surgical procedure type, in accordance with some embodiments. The computer processor 58 is configured to perform the process 1802 in accordance with some embodiments. During set up for a surgical procedure, a rules block 1804 and match block 1814 determine whether to cause a launch of a control signal based upon patient anatomical information, patient position information and surgical procedure type and rules from the first rules information structure 1012.

More particularly, during set up of mechanical support arms 72 for a surgical procedure using system 10, rules block 1804 receives patient anatomical information 1806 that can be input to the processor 58. Rules block 1804 receives patient position information obtained using position sensors 1000 and entered to the processor 58. Rules block 1804 receives surgical type information, which may include incision pattern information, for example, which is input to the processor 58.

Also, during the surgical procedure, a control signal rules storage block 1812 provides to the rules block 1804, patient anatomical feature signature information, patient position signature information and surgical procedure type information from within a first rules block portion 1012A of the first control signal rules information structure 1012. The rules block 1804 compares patient anatomical feature, patient position and surgical procedure type information provided by blocks 1806, 1808, 1810, respectively, with associated patient anatomical feature signature, patient position signature and surgical system type information from the first rules block portion 1012A. It will be appreciated that in some embodiments, the computer processor 58 is configured to transform patient anatomical feature information, patient position information and surgical procedure type information obtained by the system 10 into a format suitable for comparing against signature and state information from the first portion 1012A of the control signal rules information structure 1012. In particular, in some embodiments raw patient anatomical feature/patient position/surgical procedure type is processed to derive a classification (signal/probability) which then is looked up in a table to determine mechanical support arm positions based upon a determined classification.

Decision module 1806 determines whether a match occurs between the provided patient anatomical feature, patient position, and surgical procedure type information on the one hand and rules information from the first rules block portion 1012A on the other. It will be appreciated that in machine learning embodiments a match is determined based upon a range of similarity between patient anatomical feature, patient position, and surgical procedure type and rules information. Thus, for example, a combination of patient anatomical feature, patient position, and surgical procedure type that is within some threshold limit of a certain rule is determined to match that rule.

Block 1814, in response to determination of a match between a combination of patient anatomical feature, patient position, and surgical procedure type information and a rule, launches a control signal from within a second rules portion 1012B of the control signal rules information structure 1012 that corresponds the matching rule. For example, in response to determination that patient anatomical feature, patient position, and surgical procedure type information received during a surgical procedure matches $SigAn_2$, $SigPos_1$ and $SigSur_1$ of the first portion 1012A, block 1816 launches signal $CNTL_{ARMS1}$ from within a second portion 1012B of the control signal information structure 1012. The launched control signal has a value that corresponds to the combination of anatomical position, patient position and surgical procedure signatures that it is associated with in the information structure 1012 signatures. The control signal causes a mechanical support arms 72 to move to positions that correspond to these associated signatures. More specifically, in accordance with some embodiments, the launched control signal has a value to cause controlled movement of rotational positions of the first through third segments 72-1 to 27-3 about respective axes 91-93 and to cause controlled rotational movement of rotational positions of the first through fourth sub-segment 101-104 about respective axes 111-114.

Figure 19:
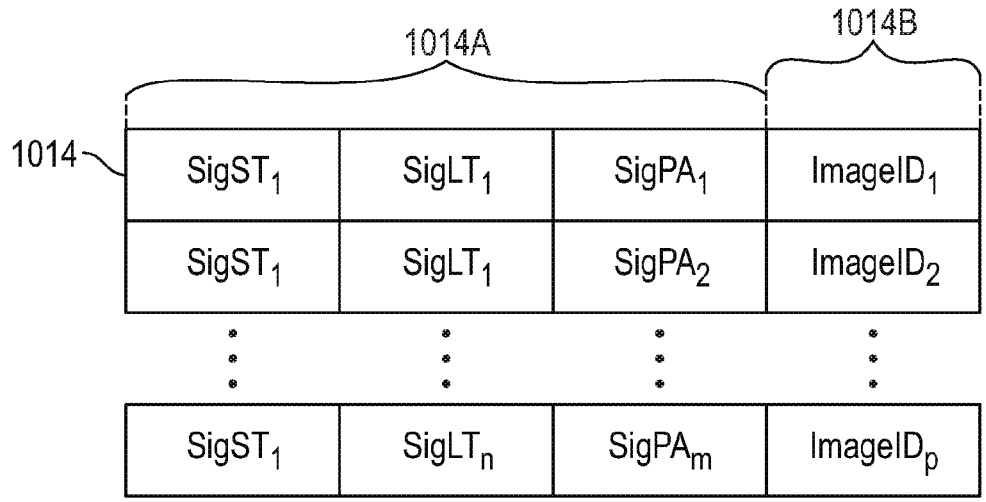
FIG. 19 is an illustrative drawing representing an example second rules information structure to associate operating room layout information and operating room personnel information with system module information, in accordance with some embodiments.

FIG. 19 is an illustrative drawing representing an example second rules information structure 1014 to associate operating room layout information and operating room personnel information with system module information, in accordance with some embodiments. The second rules are developed based upon data from prior surgeries represented in the first and third data information structures 1006, 1010. The second rules correlate patterns of operating room layout and surgical personnel activity with system module position information that may be presented on display 60 to provide guidance as to surgical system module placement during set up for a surgical procedure.

For an example first type of surgical procedure, the second rules information structure 1014 associates surgery type signatures ($SigST_1$ ... $SigST_1$), operating room layout signatures ($SigLT_1$ ... $SigLT_n$) and personnel activity signatures ($SigPA_1$ ... $SigPA_m$) with system module layout information display image identifiers ($ImageID_1$ ... $ImageID_p$) for display on display screen 60. In some embodiments, an operating room layout signature includes a multi-dimensional vector. In some embodiments, an operating room layout signature indicates fixture positions, room dimensions and mounting points and models of articulated apparatus such as boom mounted lights. In some embodiments, a personnel activity signature includes a multi-dimensional vector. In some embodiments, recorded personnel activity information includes personnel role, spatio-temporal motion trace and action history. In accordance with some embodiments, different system module positions are associated with different combinations of operating room layout signatures and operating room personnel activity signatures. In accordance with some embodiments, machine learning techniques can be used to generate the second rules. More specifically, for example, classifiers can be used together with expert knowledge to correlate operating mom layout signatures and operating room personnel activity signatures with system module positions.

Figure 20:
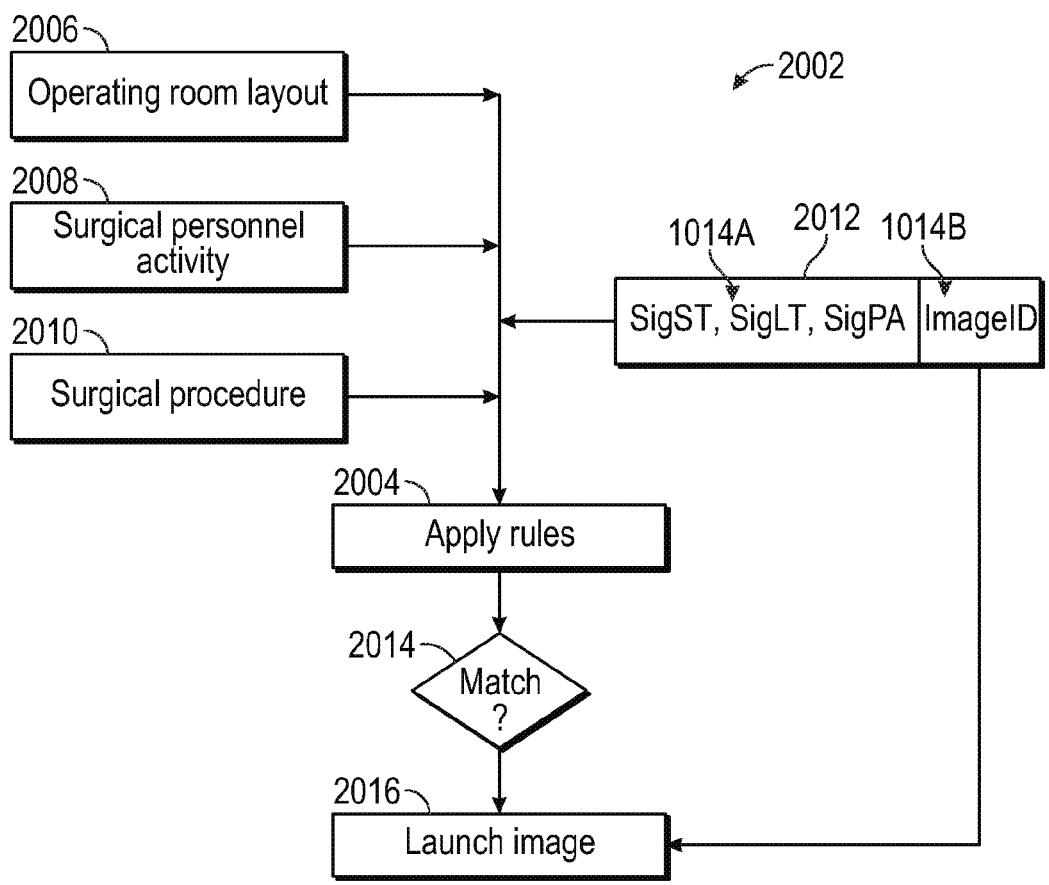
FIG. 20 is an illustrative flow diagram representing a process to produce computer display image information representing recommended system module positions based at least in part upon operating room layout information, surgical personnel activity information and surgical procedure type information, in accordance with some embodiments.

FIG. 20 is an illustrative flow diagram representing a process 2002 to produce computer display image information representing recommended system module positions based at least in part upon operating room layout information, surgical personnel activity information and surgical procedure type information, in accordance with some embodiments. The computer processor 58 is configured to perform the process 2002 in accordance with some embodiments. During set up for a surgical procedure, a rules block 2004 and match block 2014 determine whether to display an image indicative of a proposed positioning of surgical system modules based upon patient anatomical information, patient position information and surgical procedure type and rules from the second rules information structure 1014.

More particularly, during set up of surgical system modules 16, 24, 30, 54 for a surgical procedure, rules block 2004 receives operating room layout information 2006 that can be input to the processor 58. Rules block 2004 receives operating room personnel activity information entered to the processor 58. Rules block 2004 receives surgical type information, which may include incision pattern information, for example, which is input to the processor 58.

Also, during the surgical procedure, an image rules storage block 2012 provides to the rules block 2004, patient operating room layout signature information, personnel activity signature information and surgical procedure type information from within a second rules block portion 1014A of the second rules information structure 1014. The rules block 2004 compares operating room layout, surgical personnel activity information and surgical procedure type information provided by blocks 2006, 2008, 2010, respectively, with associated operating room layout signature, personnel activity signature and surgical system type information from the second rules block portion 1014A. It will be appreciated that in some embodiments, the computer processor 58 is configured to transform operating room layout information, surgical personnel activity information and surgical procedure type information obtained by the system 10 into a format suitable for comparing against signature and state information from the first portion 1014A of the control signal rules information structure 1014.

Decision module 2006 determines whether a match occurs between the provided operating room layout, personnel activity, and surgical procedure type information on the one hand and rules information from the second rules block portion 1014A on the other. It will be appreciated that in machine learning embodiments a match is determined based upon a range of similarity between operating room layout, personnel activity, and surgical procedure type and rules information. Thus, for example, a combination of operating room layout, personnel activity, and surgical procedure type that is within some threshold limit of a certain rule is determined to match that rule.

Block 2014, in response to determination of a match between a combination of operating room layout, personnel activity, and surgical procedure type information and a rule, launches an image signal from within a second rules portion 1014B of the second rules information structure 1014 that corresponds the matching rule. For example, in response to determination that operating room layout, personnel activity, and surgical procedure type information received during a surgical procedure matches $SigOR_2$, $SigAct_1$ and $SigSur_1$ of the first portion 1014A, block 2016 launches signal $IMG_{A1}$ from within a second portion 1014B of the information structure 1014. In accordance with some embodiments, an image is produced on a display screen 60 such as an image representing an operating room layout and system module positions of one of FIGS. 13A-13C, for example.

Although illustrative embodiments have been shown and described, a wide range of modification, change and substitution is contemplated in the foregoing disclosure and in some instances, some features of the embodiments may be employed without a corresponding use of other features. For example, in some embodiments, the processor 58 is coupled to a memory device such as storage device 1004 that includes an instruction set executable on the processor 58 to cause the processor 58 to perform operations. In some embodiments, the operations include determining patient position information during a setup of the surgical system for a surgical procedure. The operations further include determining a match between the determined patient position information during the setup and a respective patient position signature. The operations still further include launching, during the setup, a support arm control signal within the surgical system that corresponds to the matched respective patient position signature.

Moreover, in some embodiments the processor 58 is coupled to a memory device such as storage device 1004 that includes an instruction set executable on the processor 58 to cause the processor 58 to perform operations that include determining operating room layout information during a setup of the surgical system for a surgical procedure. The operations further include determining a match between the determined operating room layout information during the setup and a respective operating room layout signature. The operations still further include producing an image representing surgical system module position that corresponds to the matched respective operating room layout signature.

One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A method for use with a teleoperated surgical system (surgical system), the method comprising:
using one or more scan sensors to sense patient position to determine patient position information;
determining, using a processor, a match between the determined patient position information and a patient position signature;
using the one or more scan sensors to sense patient anatomical features to determine patient anatomical feature information; and
determining, using the processor, a match between the determined patient anatomical feature information and a patient anatomical feature signature; and
launching a support arm control signal based upon a stored rule for selecting the support arm control signal based upon a combination of the patient position signature and the anatomical feature signature.

2. The method of claim 1 further including:
moving a mechanical support arm to a position that corresponds to the launched control signal value.

3. The method of claim 1 further including:
moving a mechanical support arm segment to a rotational position about a horizontal axis that corresponds to the launched control signal value.

4. The method of claim 1 further including:
moving a mechanical support arm segment to a rotational position about a vertical axis that corresponds to the launched control signal value.

5. The method of claim 1,
wherein using one or more scan sensors to sense patient position and produce patient position information includes scanning with a one of a laser position sensor and an infra-red position sensor.

6. The method of claim 1 further including:
for each of a multiplicity of occurrences of a setup of one or more instances of the surgical system for performance of a surgical procedure, recording patient position information during the setup and recording support arm position information during the setup; and
determining a respective a respective patient position signature to associate with a respective support arm position based at least in part upon the recorded patient position information and the recorded support arm position information.

7. The method of claim 1 further including:
for each of a multiplicity of occurrences of a setup of one or more instances of the surgical system for performance of a surgical procedure, recording patient anatomical feature information during the setup, recording patient position information during the setup, and recording support arm position information during the setup; and
determining a respective combination of a respective patient anatomical feature signature and a respective patient position signature to associate with a respective support arm position based at least in part upon the recorded patient anatomical feature information and the recorded patient position information and the recorded support arm position information.

8. A surgical system that includes a surgical instrument and a surgical instrument actuator comprising:

one or more scan sensors to sense patient position to determine patient position information;
one or more scan sensors to sense patient anatomical features to determine patient anatomical feature information;
a surgical instrument support arm;
a processor;
a memory storage device;
wherein the memory storage device stores an instruction set executable on the processor to cause the surgical system to perform operations comprising:
determining a match between the determined patient position information and a patient position signature;
determining a match between the determined patient anatomical feature information and a patient anatomical feature signature; and
launching a support arm control signal based upon a stored rule for selecting the support arm control signal based upon a combination of the patient position signature and the anatomical feature signature.

9. The surgical system of claim 8, the operations further including:
for each of a multiplicity of occurrences of a setup of one or more instances of the surgical system for performance of a surgical procedure, recording patient position information during the setup and recording support arm position information during the setup; and
determining a respective a respective patient position signature to associated with a respective support arm position based at least in part upon the recorded patient position information and the recorded support arm position information.

10. The surgical system of claim 8 further including:
for each of a multiplicity of occurrences of a setup of one or more instances of the surgical system for performance of a surgical procedure, recording patient anatomical feature information during the setup, recording patient position information during the setup, and recording support arm position information during the setup; and
determining a respective combination of a respective patient anatomical feature signature and a respective patient position signature to associate with a respective support arm position based at least in part upon the recorded patient anatomical feature information and the recorded patient position information and the recorded support arm position information.

\* \* \* \* \*

UNITED STATES PATENT AND TRADEMARK OFFICE
CERTIFICATE OF CORRECTION

| | |
|---|---|
| PATENT NO. | : 11,406,462 B2 |
| APPLICATION NO. | : 16/349214 |
| DATED | : August 9, 2022 |
| INVENTOR(S) | : Itkowitz et al. |

It is certified that error appears in the above-identified patent and that said Letters Patent is hereby corrected as shown below:

On the Title Page

On page 2, in Column 2, under "Other Publications", Line 13, delete "Appiication" and insert --Application-- therefor Signed and Sealed this
Twenty-fifth Day of October, 2022

Katherine Kelly Vidal
*Director of the United States Patent and Trademark Office*